United States Patent
Birken et al.

(10) Patent No.: US 7,229,781 B2
(45) Date of Patent: *Jun. 12, 2007

(54) DIAGNOSTIC KIT FOR PREDICTING THE ONSET OF MENOPAUSE

(75) Inventors: Steven Birken, Dumont, NJ (US); Yacov Maydelman, Fort Lee, NJ (US); Galina I. Kovalevskaya, New York, NY (US); John F. O'Connor, New Rochelle, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 724 days.

This patent is subject to a terminal disclaimer.

(21) Appl. No.: 10/159,354

(22) Filed: May 31, 2002

(65) Prior Publication Data

US 2003/0059842 A1 Mar. 27, 2003

Related U.S. Application Data

(62) Division of application No. 09/018,122, filed on Feb. 3, 1998, now abandoned.

(51) Int. Cl.
- *G01N 33/50* (2006.01)
- *G01N 33/53* (2006.01)
- *G01N 33/536* (2006.01)
- *G01N 33/537* (2006.01)
- *G01N 33/541* (2006.01)

(52) U.S. Cl. .................. 435/7.92; 435/7.1; 435/7.5; 530/387.1

(58) Field of Classification Search ............... 435/7.1; 530/387.1
See application file for complete search history.

(56) References Cited

U.S. PATENT DOCUMENTS

| | | | | |
|---|---|---|---|---|
| 5,156,977 | A | * 10/1992 | Hirth et al. ............... | 436/548 |
| 5,976,876 | A | 11/1999 | Canfield et al. | |
| 6,521,416 | B1 | 2/2003 | Birken et al. | |
| 2002/0161198 | A1 * | 10/2002 | Canfield et al. ......... | 530/387.1 |

OTHER PUBLICATIONS

Blithe, D.L., A.H. Akar, R.E. Wehmann and B.C. Nisula, 1988. Purification of beta-core fragment from pregnancy urine and demonstration that its carbohydrate moieties differ from those of native human chorionic gonadotropin-beta. *Endocrinology* 122:173-180.

Burger, H.G., 1994b. Diagnostic role of follicle-stimulating hormone (FSH) measurements during the menopausal transition—a analysis of FSH, oestradiol and inhibin [Review]. *Eur. J. Endocrinology* 130:38-42.

Burger, H.G., P.G. Farnworth, J.K. Findlay, C.J. Gurusinghe, D.L. Healy, P. Mamers, A. Mason, and D.M. Robertson, 1995. Aspects of current and future inhibin research. [Review]. *Reprod. Fertil. Dev.* 7:997-1002.

Burger, H.G., 1996. The endocrinology of the menopause. [Review]. *Maturitas* 23:129-136.

Cole, L.A., Y. Wang, M. Elliot, M. Latif, J.T. Chambers, S.K. Chambers, P.E. Schwartz, 1988a. Urinary human chorionic gonadotropin free b-subunit and b-core fragment: a new marker of gynecological cancer. *Cancer Res* 48:1356-1360.

Cole, L.A., J.H. Nam, J.T. Chambers, P.E. Schwartz, 1990. Urinary gonadotopin fragment, a new tumor marker: II. Differentiating a benign from a malignant pelvic mass. *Gynecol. Oncol.* 36:391-394.

Cole, L.A., P.E. Schwartz, Y. Wang, 1988b. Urinary gonadotropin fragments (UGF) in cancers in the female reproductive system. I. Sensitivity and specificity, comparison with other markers. *Gynecol. Oncol.* 31:82-90.

Hee, J., J. MacNaughton, M. Bangah, H.G. Burger, 1993. Perimenopausal patterns of gonadotropins, immunoreactive inhibin, oestradiol, and progesterone. *Maturitas* 18:9-20.

Iles, R.K., C.L. Lee, I. Howes, S. Davies, R. Edwards, T. Chard, 1992. Immunoreactive beta-core-like material in normal post-menopausal urine: human chorionic gonadotrophin or LH origin? Evidence for the existence of LH core. *J. Endocrinol.* 133:459-466.

Kato, Y., G.D. Braunstein, 1988. Beta-core fragment is a major form of immunoreactive urinary chorionic gonadotropin in human pregnancy. *J. Clin. Endocrinol. Metab.* 66: 1197-1201.

Kovalevskaya, G., S. Birken, J. O'Connor, J. Schlatterer, Y. Madelman, and R. Canfield, 1995. HLH beta core fragment immunoreactivity in the urine of ovulating women: A sensitive and specific immunometric assay for its detection. *Endocrine* 3: 881-887.

Krichevsky, A., S. Birken, J. O'Connor, K. Bikel, J. Schlatterer, C. Yi, G. Agosto, and R. Canfield, 1991. Development and characterization of a new, highly specific antibody to the human chorionic gonadotropin-beta fragment. *Endocrinology* 128: 1255-1264.

Krichevsky, A., S. Birken, J.F. O'Connor, K. Bikel, J.P. Schlatterer, R.E. Canfield, 1994. The development of a panel of monoclonal antibodies to human luteinizing hormone and its application to immunological mapping and two-site assays. *Endocrine* 2: 511-520.

Lee, C.L., R.K. Iles, J.H. Shepherd, C.N. Hudson, and T. Chard. 1991. The purification and development of a radioimmunoassay for beta-core fragment of human chorionic gonadotrophin in urine: application as a marker of gynaecological cancer in premenopausal and postmenopausal women. *J. Endocrinol.* 130: 481-489.

Neven, P., R.K. Iles, C.L. Lee, C.N. Hudson, J.H. Shepherd, T. Chard, 1993. Urinary chorionic gonadotropin subunits and beta-core in nonpregnant women: A study of benign and malignant gynecologic disorders. *Cancer* 71: 4124-4130.

(Continued)

*Primary Examiner*—Marianne P. Allen
*Assistant Examiner*—Regina M. DeBerry
(74) *Attorney, Agent, or Firm*—John P. White; Cooper & Dunham LLP

(57) ABSTRACT

The present invention provides methods to quantitate the hLHβ core fragment in a sample. The present invention now makes it possible to evaluate the metabolism of hLH in premenopausal, perimenopausal and postmenopausal women and to distinguish between normal and abnormal physiological states.

6 Claims, 29 Drawing Sheets

OTHER PUBLICATIONS

Neven, P., R.K. Iles, I. Howes, K. Sharma, J.H. Shepherd, R. Edwards, W.P. Collins, T. Chard, 1993. Substantial urinary concentrations of material resembling beta-core fragment of chorionic gonadotropin beta-subunit in mid-menstrual cycle. *Clin. Chem.* 39: 1857-1860.

O'Connor, J.F., S. Birken, J.W. Lustbader, A. Krichevsky, Y. Chen, R.E. Canfield, 1994. Recent advances in the chemistry and immunochemistry of human chorionic gonadotropin: impact on clinical measurements. [Review]. *Endocr. Rev.* 15: 650-683.

O'Connor, J.F., G. Kovalevskaya, S. Birken, J.P. Schlatterer, D. Schechter, D.J. McMahon, R.E. Canfield, 1998. The expression of the urinary forms of human luteinizing hormone beta fragment in various populations as assessed by a specific immunoradiometric assay. *Human Reproduction* 13: 826-835.

O'Connor, J.F., J.P. Schlatterer, S. Birken, A. Krichevsky, E.G. Armstrong, D. McMahon, and R. E. Canfield, 1988. Development of highly sensitive immunoassays to measure human chorionic gonadotropin, its beta-subunit, and beta core fragment in the urine: application to malignancies. *Cancer Res.* 48: 1361-1366.

Santoro, N., J. Rosenberg Brown, T. Adel, and J.H. Skurnick, 1996. Characterization of Reproductive Hormonal Dynamics in the perimenopause. *J. Clin. Endo. Metab.* 81: 1495-1501.

Schroeder, H.R., C.M. Halter, 1983. Specificity of human beta-choriogonadotropin assays for the hormone and for an immunoreactive fragment present in urine during normal pregnancy. *Clinical Chemistry* 29: 667-671.

\* cited by examiner

FIG. 1

```
         1                                                                    20
Ser-Arg-Glu-Pro-Leu-Arg-Pro-Trp-Cys-His-Pro-Ile-Asn-Ala-Ile-Leu-Ala-Val-Glu-Lys-Glu-Gly
         23
-Cys-Pro-Val-Cys-Ile-Thr-Val-Asn-Thr-Thr-Ile-Cys-Ala-Gly-Tyr-Cys-Pro-Thr-Met-Met-Arg-Val
         45
Leu-Gln-Ala-Val-Leu-Pro-Pro-Leu-Pro-Gln-Val-Val-Cys-Thr-Tyr-Arg-Asp-Val-Arg-Phe-Glu-Ser-
         67
Ile-Arg-Leu-Pro-Gly-Cys-Pro-Arg-Gly-Val-Asp-Pro-Val-Val-Ser-Phe-Pro-Val-Ala-Leu-Ser-Cys-
         89
Arg-Cys-Gly-Pro-Cys-Arg-Arg-Ser-Thr-Ser-Asp-Cys-Gly-Gly-Pro-Lys-Asp-His-Pro-Leu-Thr
         111
Cys-Asp-His-Pro-Gln-Leu-Ser-Gly-Leu-Leu-Phe
```

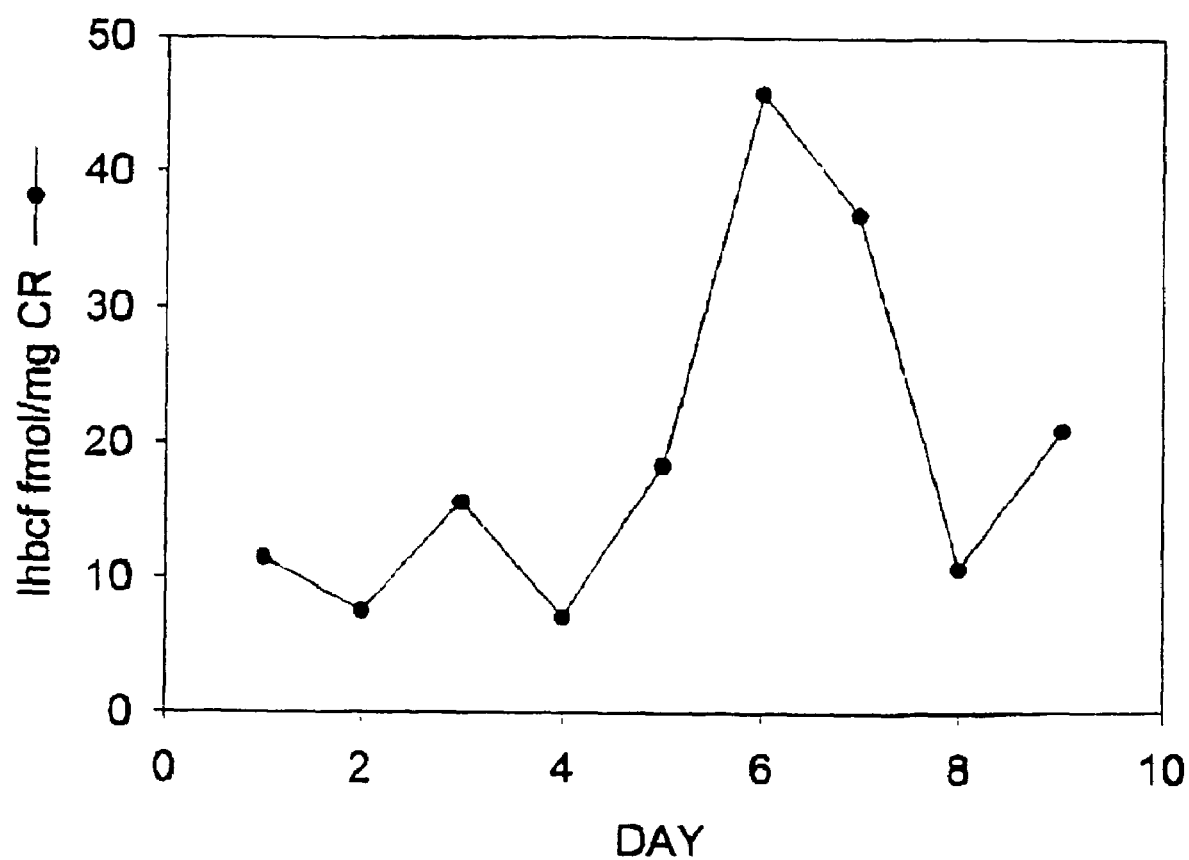

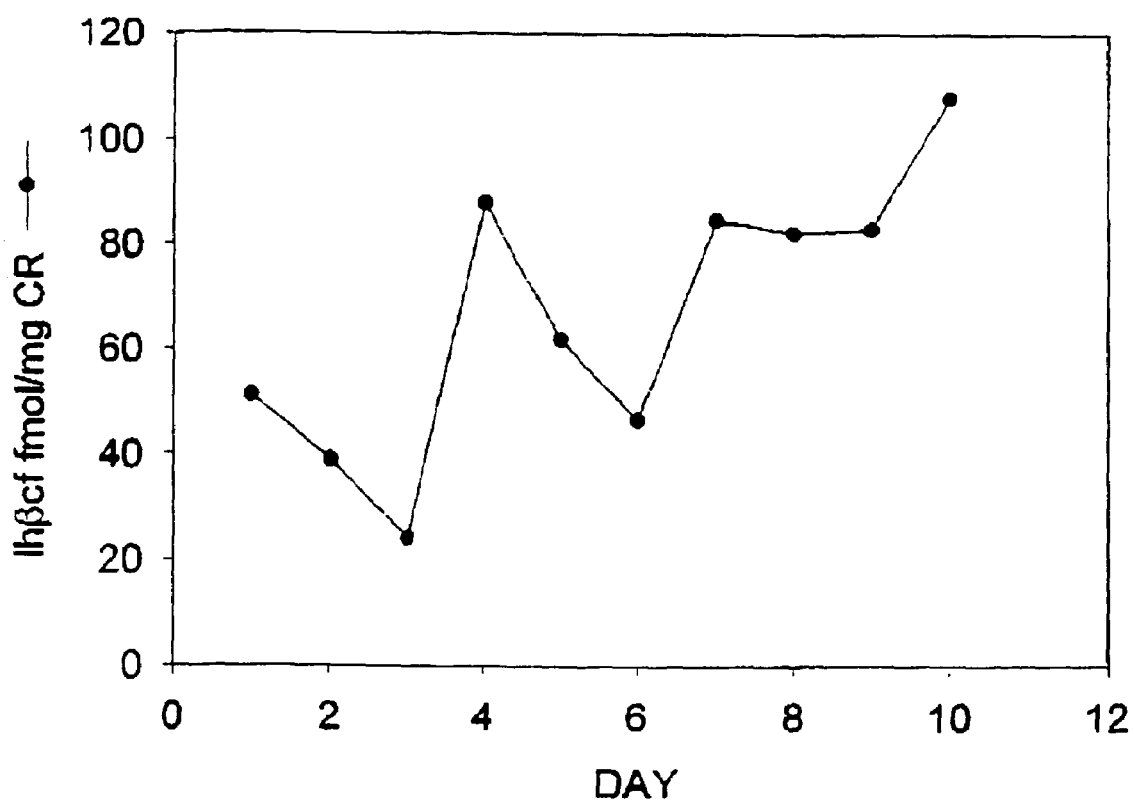

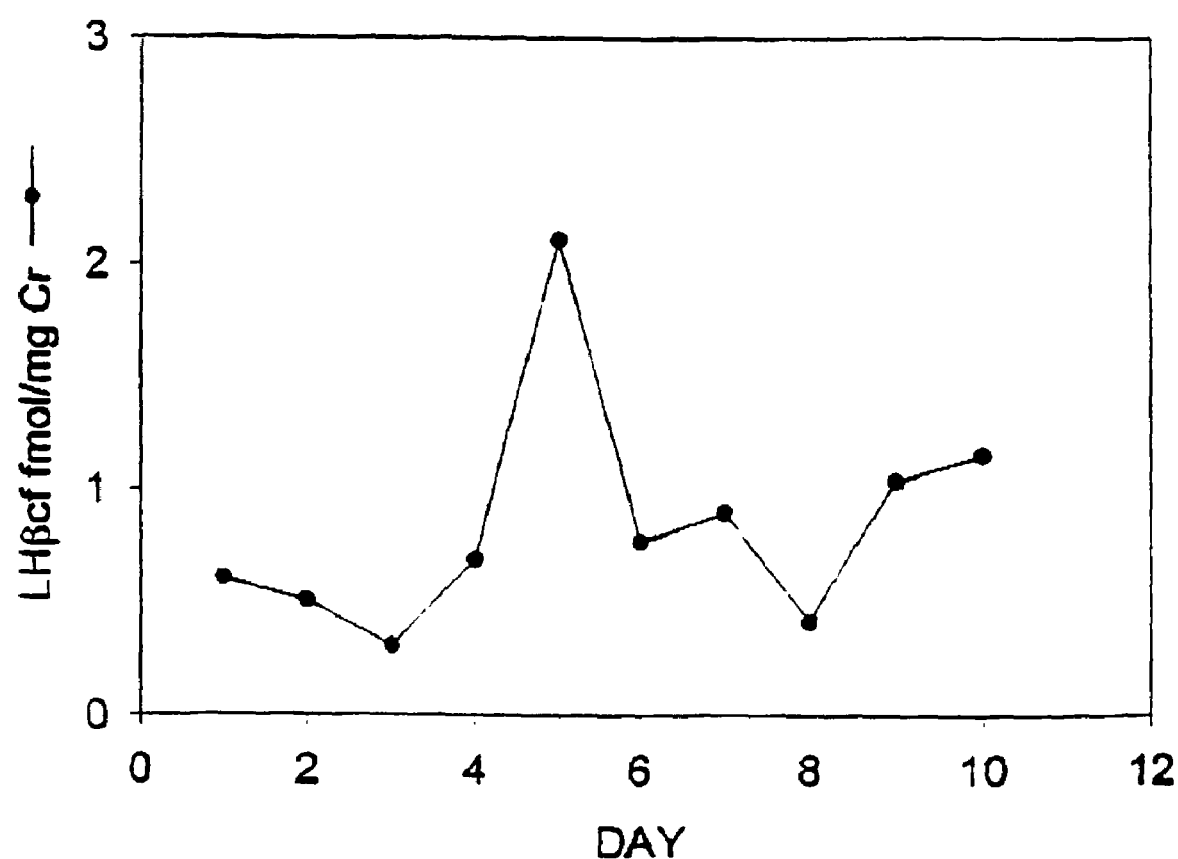

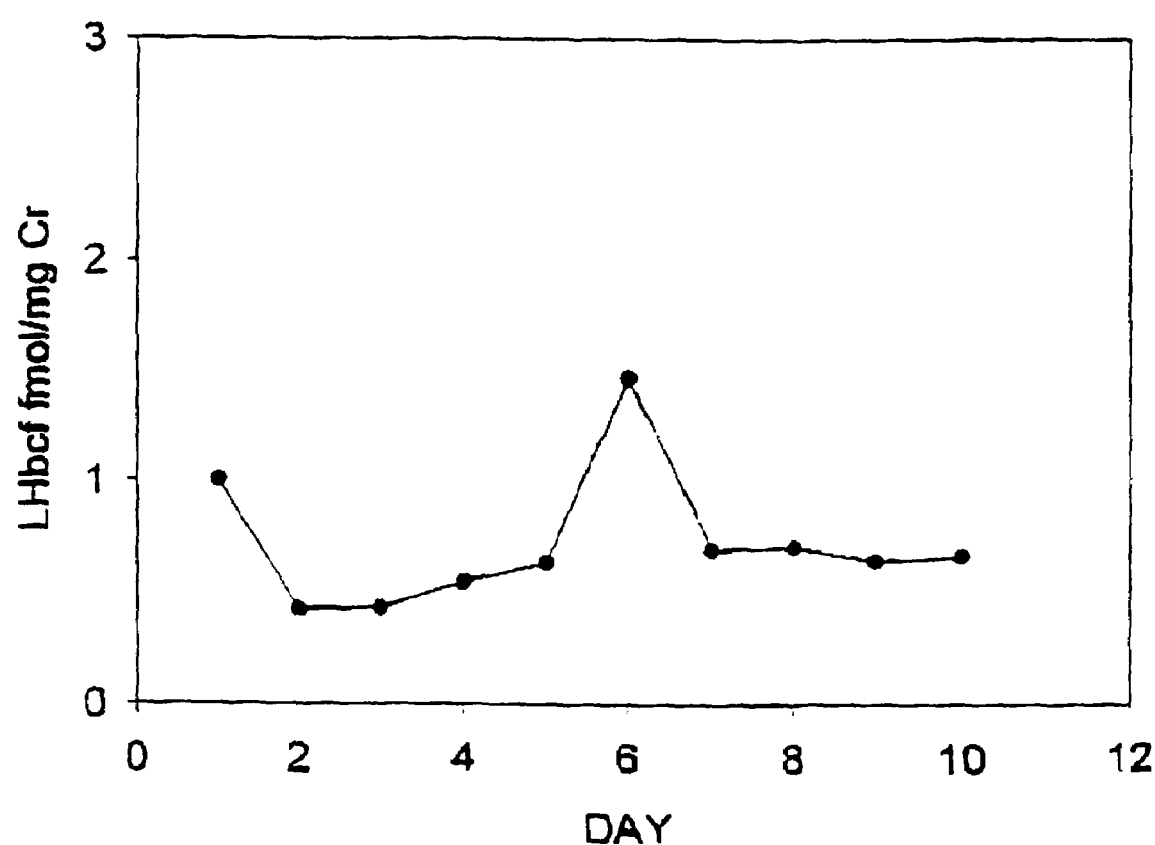

AE FMV Postmenopausal Urines

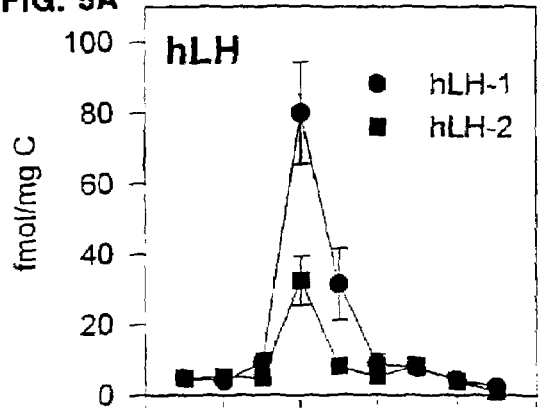
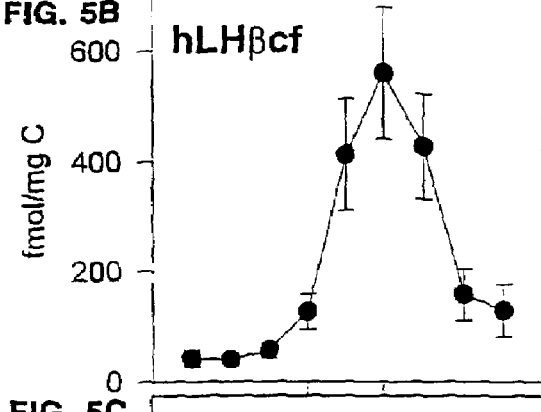
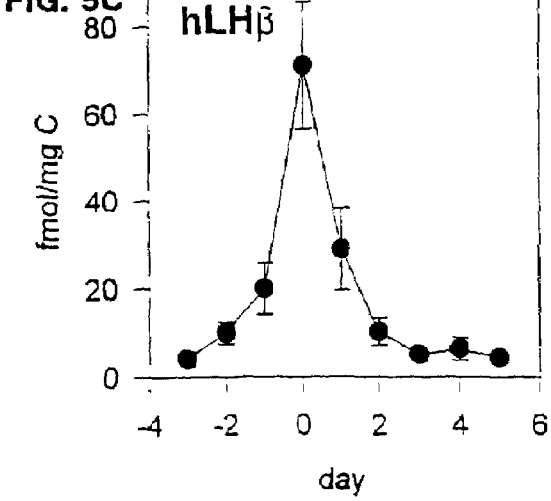
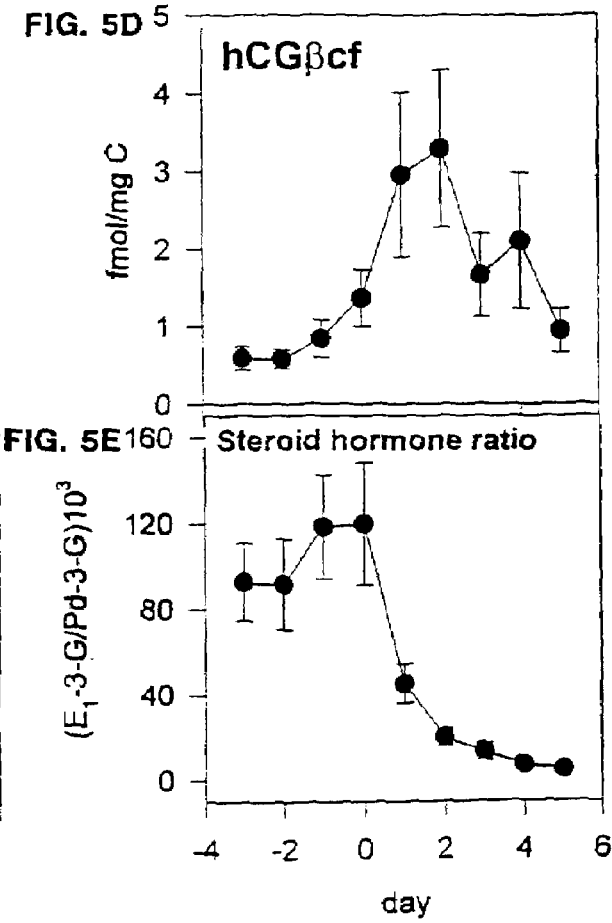

FIG. 7A Patient #67-5

FIG. 7C Patient #75-3

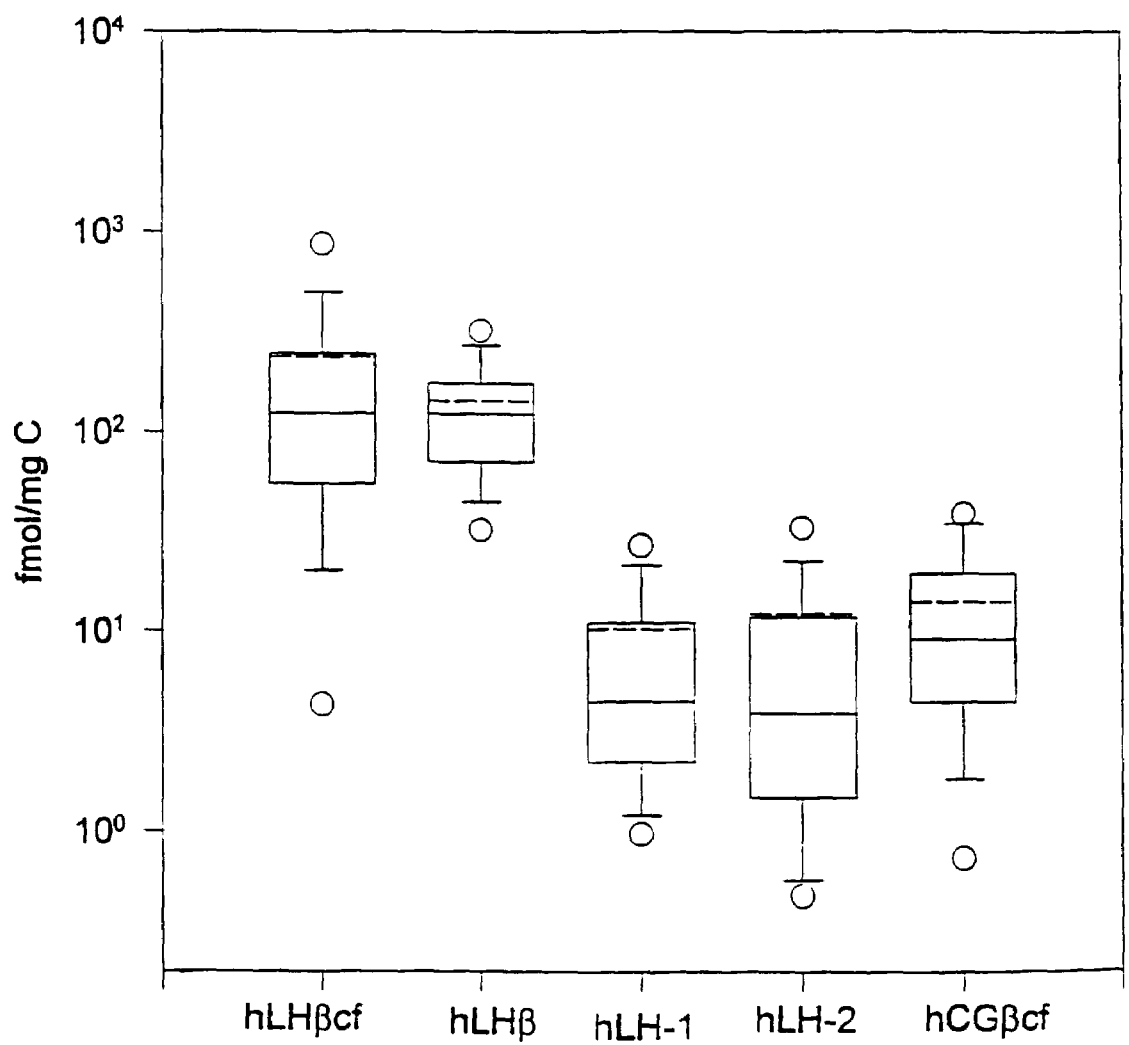

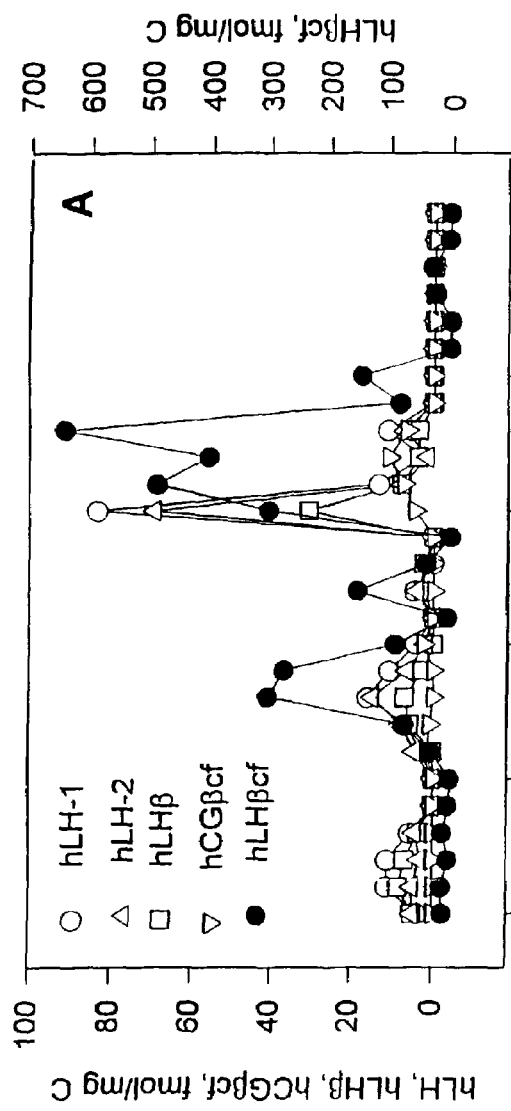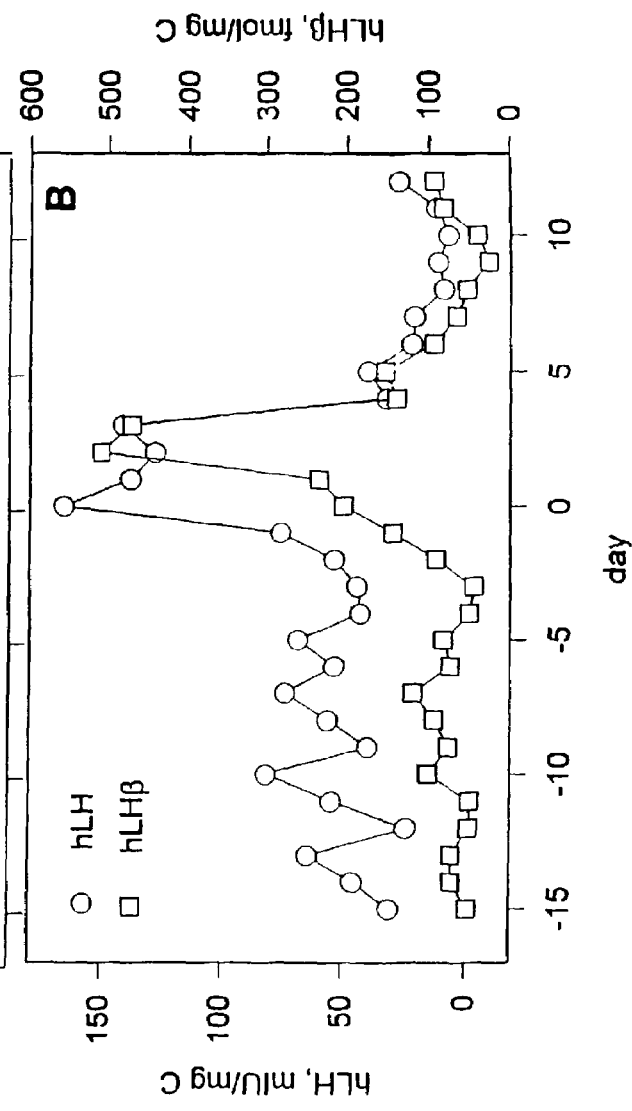
FIG. 9A
FIG. 9B

DAY of URINE COLLECTION (Random)

DAY of Urine Collection (Random FMV)

LK FMV Urines After ERT

Area = 1650

VP FMV Urines Before ERT

Area = 1350

VP FMV Urines After ERT

Area = 280

NP FMV Urines After ERT

Area = 3260

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 122 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Pro Gln Leu Ser Gly Leu Leu Phe
        115                 120

(2) INFORMATION FOR SEQ ID NO: 2:

(i) SEQUENCE CHARACTERISTICS:
       (A) LENGTH: 80 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Arg Pro Trp Cys His Pro Ile Asn Ala Ile Leu Ala Val Glu Lys Glu
1               5                   10                  15

Gly Cys Pro Val Cys Ile Thr Val Asn Thr Thr Ile Cys Ala Gly Tyr
            20                  25                  30

Cys Pro Thr Leu Pro Pro Leu Pro Gln Val Val Cys Thr Tyr Arg Asp
        35                  40                  45

Val Arg Phe Glu Ser Ile Arg Leu Pro Gly Cys Pro Arg Gly Val Asp
    50                  55                  60

Pro Val Val Ser Phe Pro Val Ala Leu Ser Cys Arg Cys Gly Pro Cys
65                  70                  75                  80

DIAGNOSTIC KIT FOR PREDICTING THE ONSET OF MENOPAUSE

This application is a divisional of U.S. Ser. No. 09/018,122, filed Feb. 3, 1998, now abandoned, the content of which is hereby incorporated into this application by reference.

The invention disclosed herein was made with Government support under NIH Grant Nos. HD15454, ES07589 and M01-RR00645. Accordingly, the U.S. Government has certain rights in this invention.

Throughout this application, various publications are referenced by author and date. Full citations for these publications may be found listed alphabetically at the end of the specification immediately preceding the Sequence Listing and the claims. The disclosures of these publications in their entireties are hereby incorporated by reference into this application in order to more fully describe the state of the art as known to those skilled therein as of the date of the invention described and claimed herein.

BACKGROUND OF THE INVENTION

With the extension of the human life span, women spend one-third of their lives beyond the reproductive years. The transition into menopause, a normal process of aging, is associated with physical risks and psychological adjustments. It is critical to improve understanding of the these changes. However, there is a lack of diagnostic tools for monitoring the temporal stages in the history of menopause despite the importance of this transition period. There is no reliable test to determine how close a woman is to menopause. Clinical decisions for treatment of perimenopausal women today are based chiefly upon subjective symptoms rather than objective diagnostic tests.

There is a lack of adequate chemical markers for defining the menopausal state since neither serum gonadotropins, estradiol, nor inhibin A or B levels are adequate for diagnosis unless daily sampling is performed for prolonged periods of time (Burger, 1996;. Burger, et al., 1995; Burger, 1994a; Burger, 1994b; Hee, et al. 1993; Metcalf, 1988). A number of studies of women during the periovulatory period have indicated that the currently used biochemical markers of menopause are inadequate (Burger, 1996;. Burger, et al., 1995; Burger, 1994a; Burger, 1994b; Hee, et al. 1993; Metcalf, 1988; Santoro, et al. 1996). Gonadotropin levels fluctuate from postmenopausal concentrations back down to levels found in normal, young cycling women (Burger, 1996; Burger, et al., 1995; Burger, 1994a; Metcalf, 1988; Metcalf, et al. 1982; Metcalf and Donald, 1979). What appear to be normal ovulatory cycles may follow prolonged anovulatory periods coincident with postmenopausal concentrations of follicle stimulating hormone (FSH) and luteinizing hormone (LH) (Burger, 1996;. Burger, et al., 1995; Burger, 1994a; Burger, 1994b; Metcalf, 1988; Metcalf, and Donald, 1979; Metcalf, et al. 1981a). Some investigators declare that all current biochemical measurements have little predictive value during the menopausal transition because of the great variations in levels of steroids and gonadotropins. (Burger, 1996;. Burger, 1994a; Burger, 1994b; Hee, et al. 1993;. Metcalf, and Donald, 1979; Metcalf, et al. 1981b; Metcalf, 1979).

Although elevations in certain serum gonadotropin levels reflecting gametogenic failure usually occur several years before a decline in estrogen and irregular cycling begins, measurement of serum gonadotropin levels, estrogen, and inhibins A and B have limited value to the practicing physician. A reliable test is essential to differentiate a premenopausal woman from a woman very early in perimenopause or the latter from one in the middle of the transition; menopausal changes could be placed in relation to the stage of menopausal transition. This would help to resolve, for example, whether treatment for osteoporosis should begin much earlier or that hormone replacement therapy should begin at a different time rather than based on symptomatic discomfit. The present invention solves these problems by providing urinary-based immunoassay methods and assay kits.

Human gonadotropins undergo metabolic transformations, which result in the presence of several smaller, structurally and immunologically related forms in the urine. A major form of urinary hCG-associated immunoreactivity is an epitope on a molecule smaller than heterodimeric hCG (Birken et al., 1996; O'Connor et al., 1994; Schroeder and Halter, 1983). This molecule has been identified as an hCG beta core fragment (hCGβcf) (Birken et al., 1988; Blithe et al., 1988). In normal pregnancy, the core fragment constitutes a major mole fraction of urinary hCG excretion (Kato and Braunstein, 1988). Using polyclonal antisera raised against hCGβcf, immunoreactive beta core like activity can be detected in both postmenopausal women and in the periovulatory period of the normal menstrual cycle (Iles et al., 1992; Neven et al., 1993). However, some immunoreactivity results from cross-reactivity with the polyclonal hCGβcf antibodies. An hLH beta core fragment (hLHβcf) has been isolated from human pituitaries and a panel of monclonal antibodies has been generated (Birken et al., 1993a; Kovalevskaya et al., 1995).

The corresponding urinary fragment is inferred from mass spectral and immunochemical analysis of chromatographically separated urinary forms. Physico-chemical characteristics, primarily mass spectral and chromatographic, indicate that the pituitary and urinary forms of hLHβcf have a different structure, probably in the carbohydrate moieties. The carbohydrate moiety of the pituitary hLHβcf resembles that of pituitary hLHβ rather than displaying the degraded carbohydrate chains present in urinary hCGβcf. The endogenous urinary core material is extremely stable to repeated freeze/thaw cycles and prolonged storage at 4° C. or at room temperature. HLHβcf cross-reaction with some hLH or hLHβ monoclonal antibodies may well interfere with the accurate estimation of the day of hLH surge when urinary tests are utilized. The expression of hLHβcf in the urine of both reproductive and postreproductive age women and in men, is now characterized employing assays highly specific for the pituitary form of the fragment.

Analysis of the metabolites of the gonadotropins excreted into urine can help to distinguish between healthy and abnormal physiological states. For example, the hCG β core fragment (hCGβcf) is present at high levels in the urine of normal pregnant women (Kato et al., 1988) but, also, occurs abnormally in the urine of nonpregnant patients with a variety of malignancies (O'Connor et al., 1988, Cole et al., 1988a, 1988b, 1990). Until now, it has not been possible to distinctly measure one of the fragments in the presence of the others. For example, the utility of the hCGβcf molecule as a marker of malignancies in postmenopausal women has been compromised by the cross-reactions of antibodies elicited to the hCGβcf with a molecule of similar structure and size (presumably the homologous fragment of hLH) excreted by normal postmenopausal women in their urine. Consequently, the high threshold measurement compromised the ability of hCGβcf to serve as a cancer marker in this important patient population. Distinguishing hLHβcf from an hCGβcf, therefore, is of great value. A preponderance of hLHβcf may indicate a normal state while a major mole fraction of the hCG fragment may be associated with malignancy (Birken et al., 1993b). The present invention provides a method to make such a distinction. Immunological analysis of the hLHβcf in normal cycling women, as compared with infertile patients, may identify a metabolic marker associated with an abnormal state (i.e.an ovulatory cycles, polycystic ovarian disease). Antibodies to the hLHβcf, isolated from pituitary extract, can also be used to measure such a molecule in urine.

Methods for specific immunometric assays which report the levels of expression of this new hLH molecular form, hLHβcf, in men and women at different stages of their reproductive history are described herein. The present invention now makes it possible to evaluate the metabolism of hLH in premenopausal, perimenopausal and postmenopausal women and in men and to distinguish between normal and abnormal physiological states.

In addition, these methods to visualize LH fragment in plasma differentiates LH fragment derived directly from pituitary from that derived by peripheral cleavage of LH. hLHβcf may circulate in plasma.

The methods described herein measure the stable metabolic products of LH which are excreted into urine usually at much higher concentrations than the parent hormones, themselves, are found in urine or blood. These assays do not use heterodimeric hormones which are unstable, unless supplemented by stabilizers such as glycerol, because they dissociate into their constituent, non-covalently bound subunits, especially under acid conditions or upon freeze thaw cycles. Urinary metabolic forms represent end-products of a degradative process. The forms explored have proven to be stable unlike the parent hormones which can dissociate into free subunits greatly complicating urinary measurements. Antibodies specific for hLH beta core fragment some of which are referred to in the present application, have been detailed in the related co-pending U.S. application Ser. No. 08/763,669 filed Dec. 11, 1996, the content of which is hereby incorporated by reference.

In particular, related co-pending U.S. application Ser. No. 08/763,669 filed Dec. 11, 1996, describes monoclonal antibody designated B505. The hybridoma cell lines for producing the antibody designated B505 and an antibody designated B503 were deposited pursuant to and in satisfaction of the requirements of the Budapest Treaty on the International Recognition of the Deposit of Microorganisms for the Purposes of Patent Procedure with the American Type Culture Collection (ATCC), 10801 University Boulevard, Manassas Va. 20110-2209, on Dec. 11, 1995 under ATCC Designation Nos. 12000 and 11999, respectively. All restrictions upon public access to these documents shall be removed upon the grant of a patent on this application and the deposit shall be replaced if viable samples cannot be made by the depository named hereinabove.

The present invention takes advantage of the natural metabolic processing of LH as a means of improving the diagnosis of women in perimenopause as well as to assess patterns of metabolites useful for monitoring estrogen replacement therapy.

An antibody, designated B152, produced by the hybridoma cell accorded ATCC Accession number HB-12467, generated against a nicked form of hCG isolated from a choriocarcinoma patient, but not specific for nicked isoform hCG is able to discriminate among carbohydrate variants of hCG. B152 is specific for an early pregnancy associated molecular isoform of hCG.which in the first four weeks of pregnancy is measured at much higher quantities than the hCG standard isoforms measured by the usual heterodimeric hCG assays exemplified by a previously decribed B109 based assay. Later in pregnancy, the B152 isoform declines and is lower in third trimester pregnancy urine than the standard isoforms measured by B109.

Because of its presence in urine, measurement of hLHβcf greatly adds to the sensitivity of measurements for the presence of related molecules in early pregnancy as well as in malignancies, including malignancies in postmenopausal women and non-trophoblastic cancers. Its measurement may be useful for prediction of Down's syndrome pregnancies and ectopic pregnancies. The core fragment of hLHβ is useful as a urinary marker for many different physiological states including disease, as markers of the state of senescence the ovary.

SUMMARY OF THE INVENTION

This invention provides a method for predicting onset of menopause for a female subject by determining the amount of hLHβcf or hLHβcf-related molecule in a sample comprising (a) contacting the sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for known postmenopausal female subject(s) or (ii) the amount determined for known premenopausal female subject(s), wherein amounts of hLHβcf or hLHβcf-related molecule in the sample similar to amounts of hLHβcf or hLHβcf-related molecule in the known postmenopausal samples indicates temporal proximity to onset of menopause, amounts of hLHβcf or hLHβcf-related molecule in the sample similar to amounts of hLHβcf or hLHβcf-related molecule in the known premenopausal samples indicates temporal distance to onset of menopause for the subject.

This invention also provides a method for predicting onset of menopause for a female subject by determining the amount of hLHβcf or hLHβcf-related molecule in a urinary sample comprising (a) contacting a capturing antibody which specifically binds to hLHβcf without substantially cross-reacting with hLH, hLHβ or hCGβcf with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with an antibody which specifically binds to hLHβcf without cross reacting with hLH, hLHβ or hCGβcf under conditions permitting binding of antibody and antigen in the sample; (e) measuring the amount of bound antibody on the bound matrix, thereby determining the amount of hLHβ or hLHβcf-related molecule in the sample; and (f) comparing the amount of hLHβcf or hLHβcf-related molecule in the sample determined in step (e) with either (i) the amount determined for known postmenopausal female subject(s) or (ii) the amount determined for known premenopausal female subject(s), wherein amounts of hLHβcf or hLHβcf-related molecule in the sample similar to amounts of hLHβcf or hLHβcf-related molecule in the known postmenopausal samples indicates temporal proximity to onset of menopause, amounts of hLHβcf or hLHβcf-related molecule in the sample similar to amounts of hLHβcf or hLHβcf-related molecule in the known premenopausal samples indicates temporal distance to onset of menopause for the subject.

This invention further provides a method for determining the onset of menopause of a female subject comprising (a) obtaining samples from the female subject; and (b) determining the amount of hLHβcf or hLHβcf-related molecule in the samples, the stable presence of elevated levels of basal hLHβcf indicating onset of menopause in the subject.

This invention additionally provides a method for assessing ovarian function in a subject by determining the amount of hLHβcf or hLHβcf-related molecule in a sample comprising (a) contacting the sample with an antibody which specifically binds to hLHβcf without substantially cross-reacting with hLH, hLHβ or hCGβcf under condition permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for subject(s) with normal ovarian function or (ii) the amount determined for subject(s) with abnormal ovarian function, wherein amounts of hLHβcf or hLHβcf-related molecule in the sample similar to amounts of hLHβcf or hLHβcf-related molecule in the samples from subjects having normal ovarian function indicates normal ovarian function, amounts of hLHβcf or hLHβcf-related molecule in the sample similar to amounts of hLHβcf or hLHβcf-related molecule in the samples from subjects having abnormal ovarian function indicates abnormal ovarian function for the subject.

In addition, this invention provides a method for determining the efficacy of hormone replacement therapy in a subject by determining the amount of hLHβcf or hLHβcf-related molecule in a sample comprising (a) contacting a sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for pre-treatment sample(s) or (ii) the amount determined for prior treatment sample(s) or (iii) the amount determined for known premenopausal sample(s) or (iv) the amount determined for known postmenopausal sample(s), wherein changes in the amount of hLHβcf or hLHβcf-related molecule in the sample indicates efficacy of the hormone replacement therapy for the subject; amounts of hLHβcf or hLHβcf-related molecule in the sample similar to amounts of hLHβcf or hLHβcf-related molecule in the known premenopausal samples indicates efficacy of the hormone replacement therapy for the subject; amounts of hLHβcf or hLHβcf-related molecule in the sample similar to amounts of hLHβcf or hLHβcf-related molecule in the known postmenopausal samples indicates lack of efficacy of the hormone replacement therapy for the subject.

Further, this invention provides a method of predicting pregnancy outcome in a subject by determining the amount of hLHβcf or hLHβcf-related molecule in a sample comprising (a) contacting a sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for pregnant subject(s) or (ii) the amount determined for non-pregnant subject(s), wherein amounts of hLHβcf or hLHβcf-related molecule in the sample similar to amounts of hLHβcf or hLHβcf-related molecule in the pregnant samples indicates a positive outcome, amounts of hLHβcf or hLHβcf-related molecule in the non-pregnant samples indicates a negative outcome of pregnancy for the subject.

Finally, this invention provides a diagnostic kit for determining the onset of menopause for a female subject comprising (a) an antibody which specifically binds to hLHβcf without substantially cross-reacting with hLH, hLHβ or hCGβcf; (b) a solid matrix to which the antibody is bound; and (c) reagents permitting the formation of a complex between the antibody and a sample.

BRIEF DESCRIPTION OF THE FIGURES

FIG. 1.

The hLH β core fragment isolated from human pituitary extracts. Antibodies were developed to this pituitary hLH β core fragment which recognize an homologous fragment of 10K MW in postmenopausal and perimenopausal as well as periovulatory urine. (Seq. ID. No.:1). Cleaved bonds are indicated by the arrows. Peptide portions deleted from the structure are in bold and crossed out. The remaining peptides are represented as Seq. ID. No.:2.

FIG. 2.

Reverse phase high pressure liquid chromatography (HPLC) separation of periovulatory and postmenopausal urine fractions which contain hLHβcf activity and pituitary hLHβcf. All fractions assayed in B505–B503 assay. The open circles denote the elution position of hLHβcf derived from the pituitary. The closed circles and squares denote the elution positions of hLHβcf partially purified from urine.

The difference in elution positions suggests a structural difference between the urinary and pituitary forms. The pituitary form elutes later while the urinary form in postmenopausal and premenopausal women elutes in identical positions. The pituitary form contains carbohydrate and sulfate similar to hLHβ. However, the urinary form may have trimmed carbohydrate.

FIGS. 3A–3K.

Figure 3C:
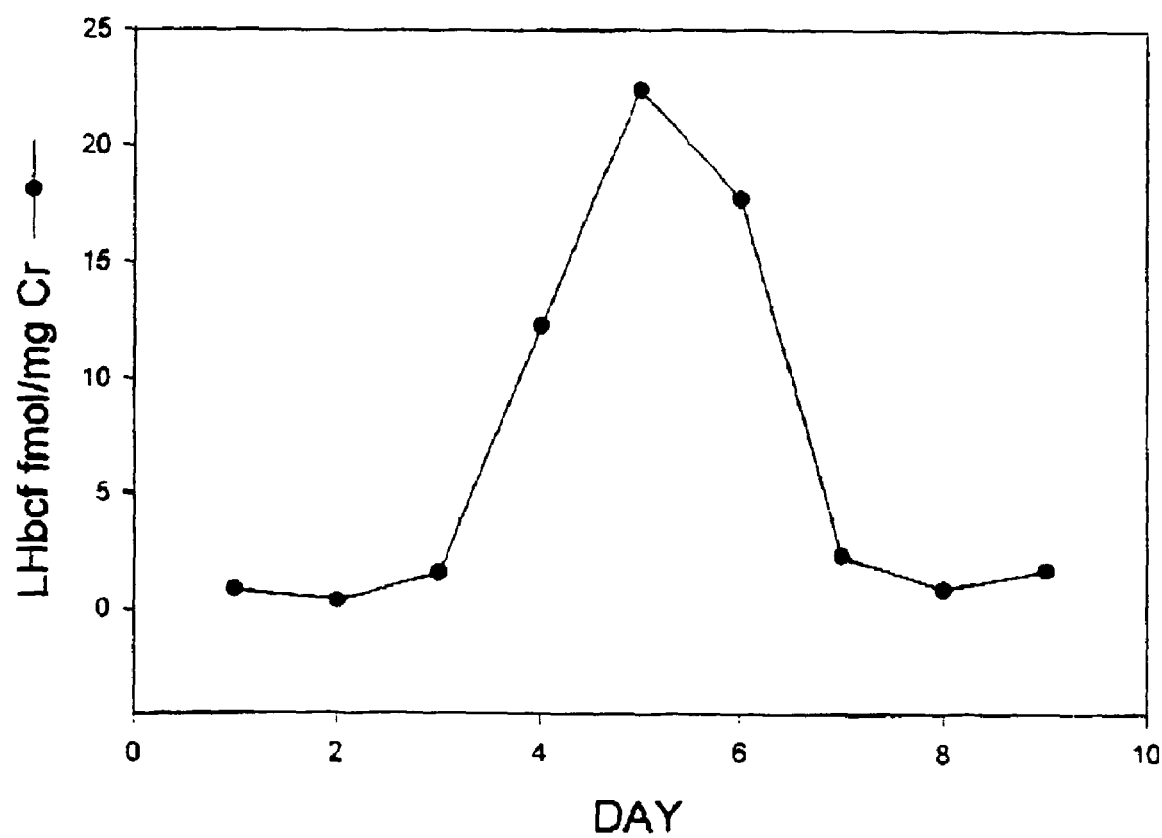
Figure 3F:
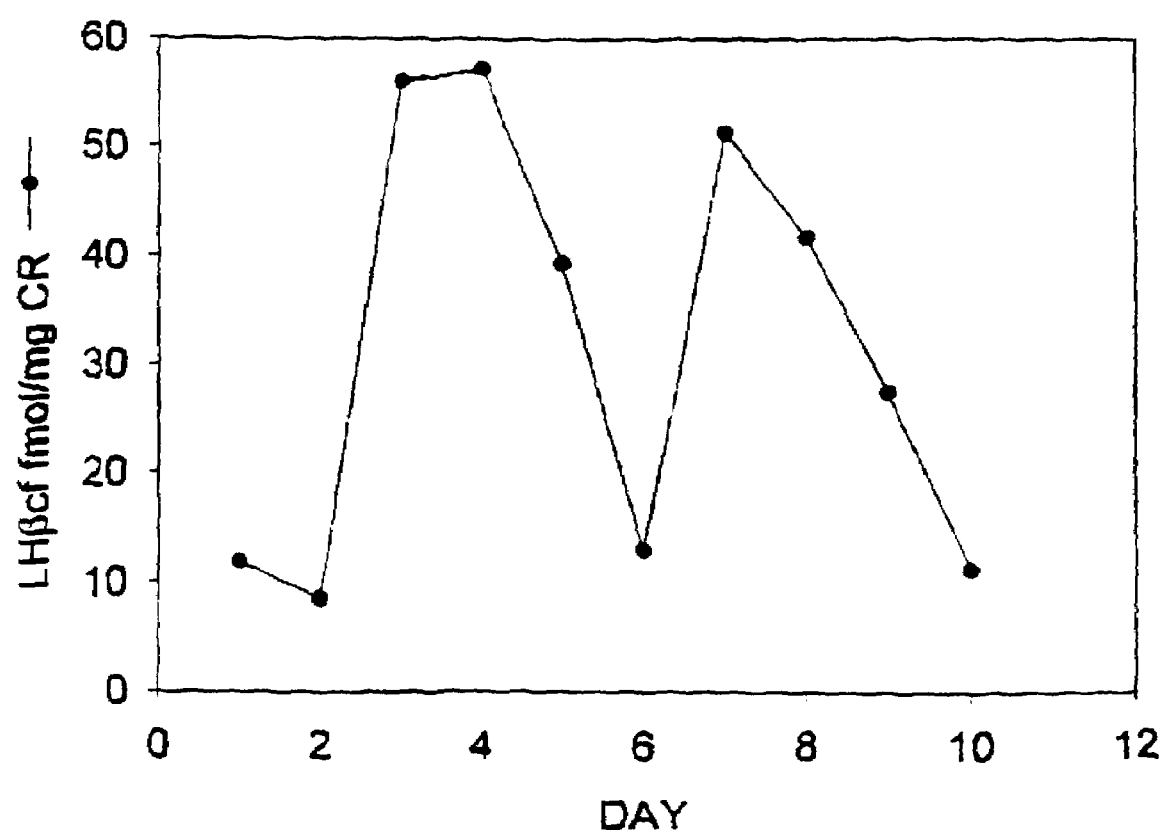
Figure 3G:
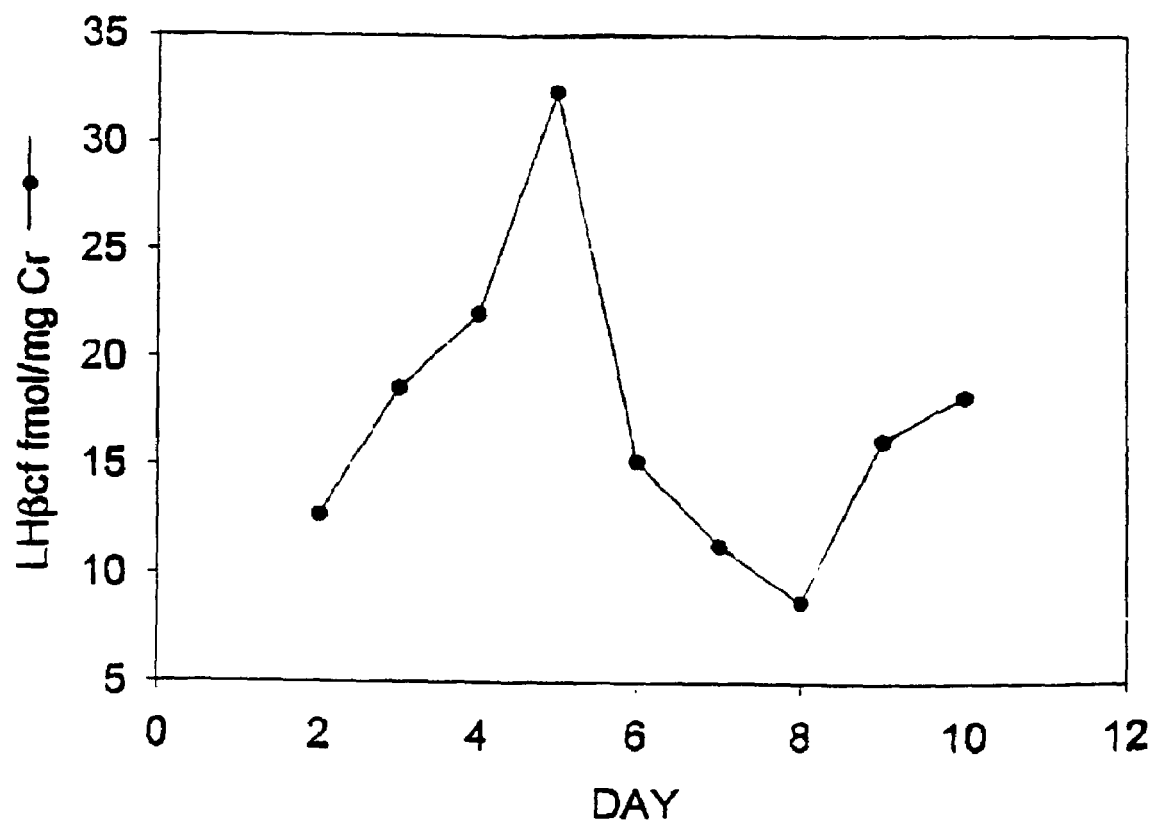
Figure 3H:
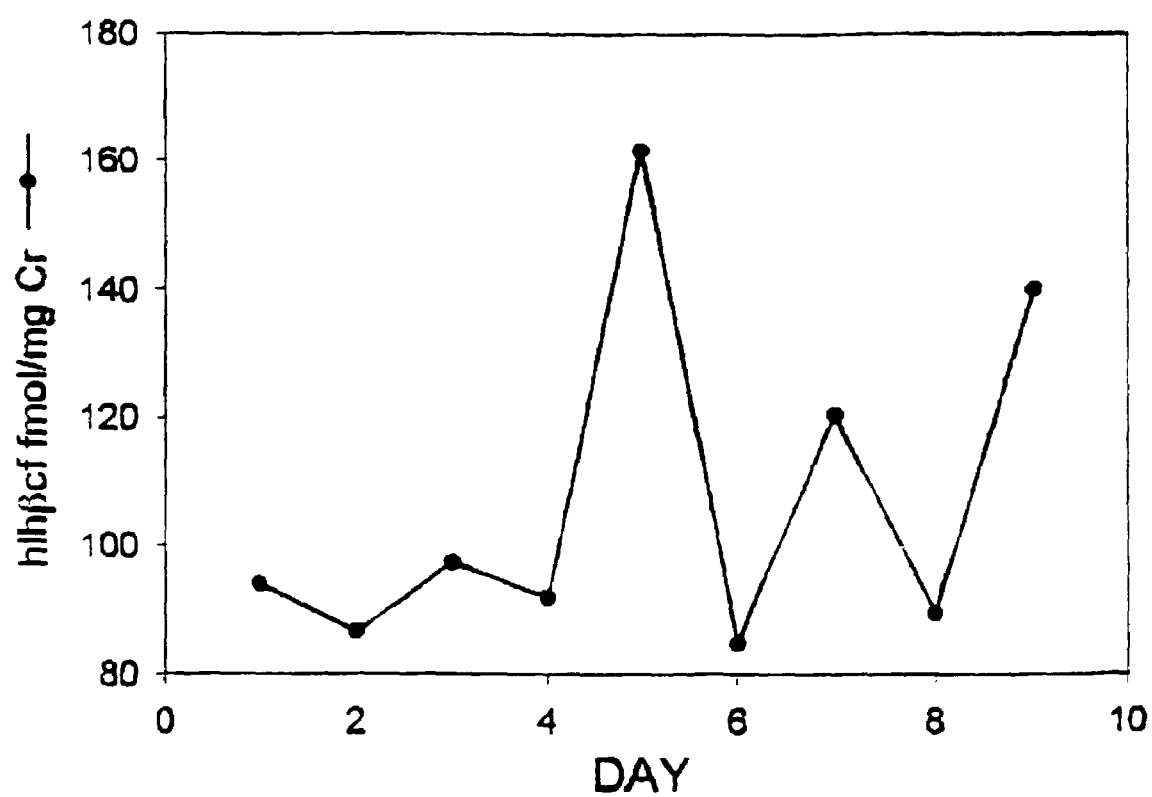
Figure 31:
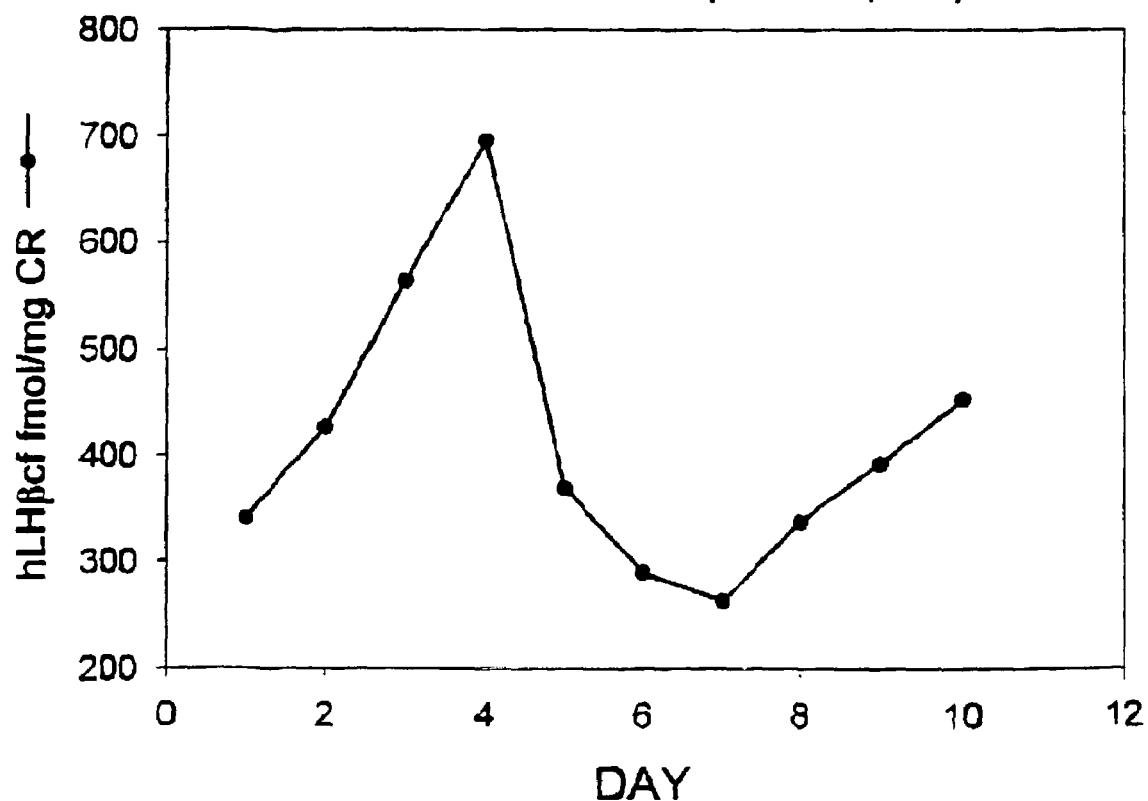
Figure 3J:
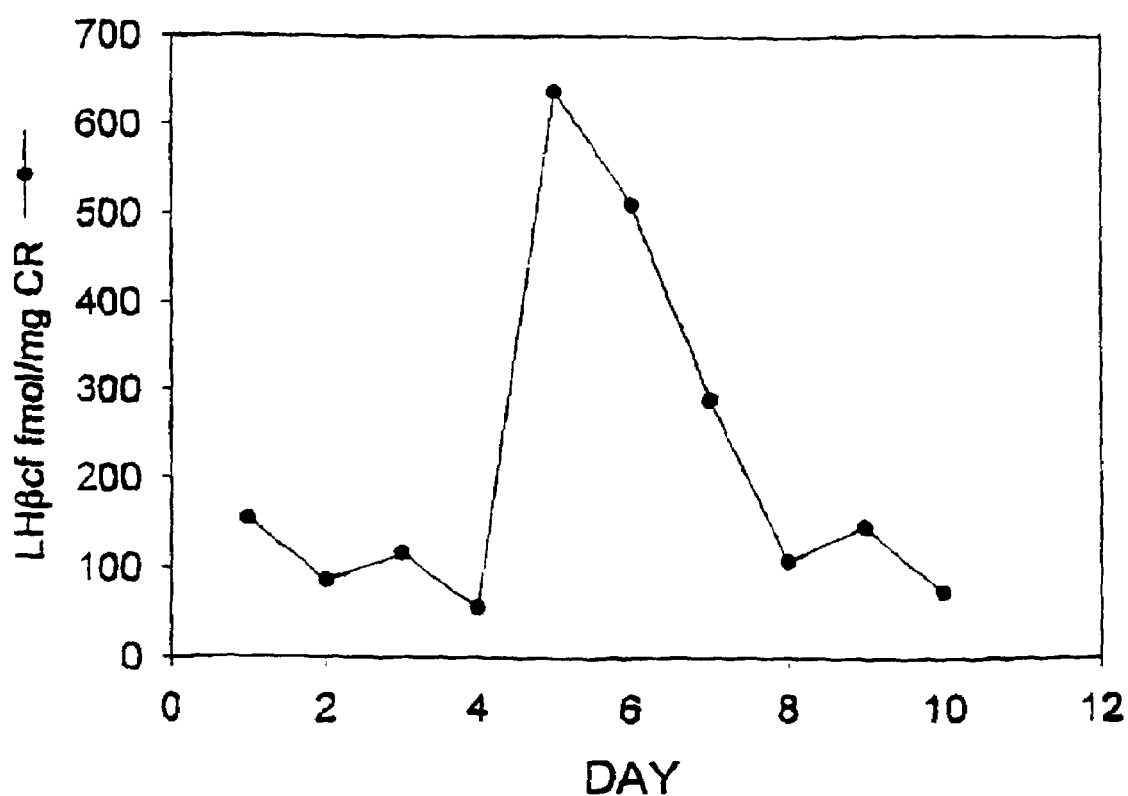
Figure 3K:
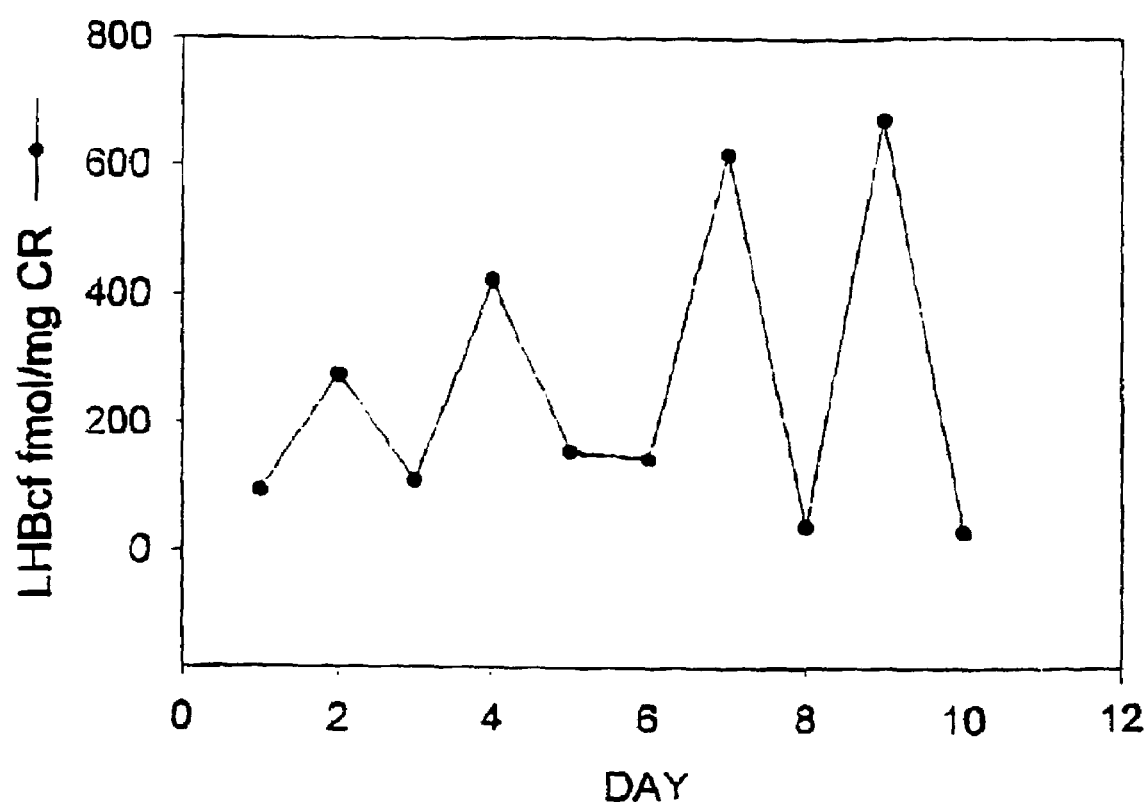

Measurements of the concentration of hLHβcf in the first morning void urine of seven premenopausal (FIGS. 3A–3G), two perimenopausal women (FIGS. 3H–3I) and two postmenopausal women (FIGS. 3J–3K). The premenopausal women were measured from the first day of menses.

FIG. 4.

Typical hLHβcf pattern observed in the first morning void urines of a postmenopausal woman analyzed for 60 days. The assay was repeated weeks later after freeze-thaws. Concentrations and patterns observed were the same as for freshly collected urine specimens. Similar collections from four patients with premature ovarian failure exhibited very similar profiles for this metabolite, except with generally higher concentrations.

FIGS. 5A–5E.

Hormone profiles in the urine of normally cycling women (n=15). Concentrations were presented as mean +/− standard error (SE), fmol/mg creatinine (fmol/mg C). hLH concentration was measured using two different IRMAs (n=8 for hLH-2 assay). Steroid hormone ratio was calculated using estrone-3-glucuronide ($E_1$-3-g) and pregnandiol-3glucuronide (Pd-3-G)×$10^3$ X. Day 0 is the day of hLH surge.

FIG. 6.

Box plot of urinary hLHβcf values in the first ten days of cycle for ten normally cycling women. Day 1 is the first day of menses. The Box extends to the 25th and 75th percentile. The upper and lower bars indicate the 90th and 10th percentile respectively. The upper and lower symbols indicate 95 and 5 percentile points respectively. The solid line inside the box marks the value of the 50th percentile. The dashed line represents the mean of concentration.

FIGS. 7A–7D.

Figures 7B, 7D:
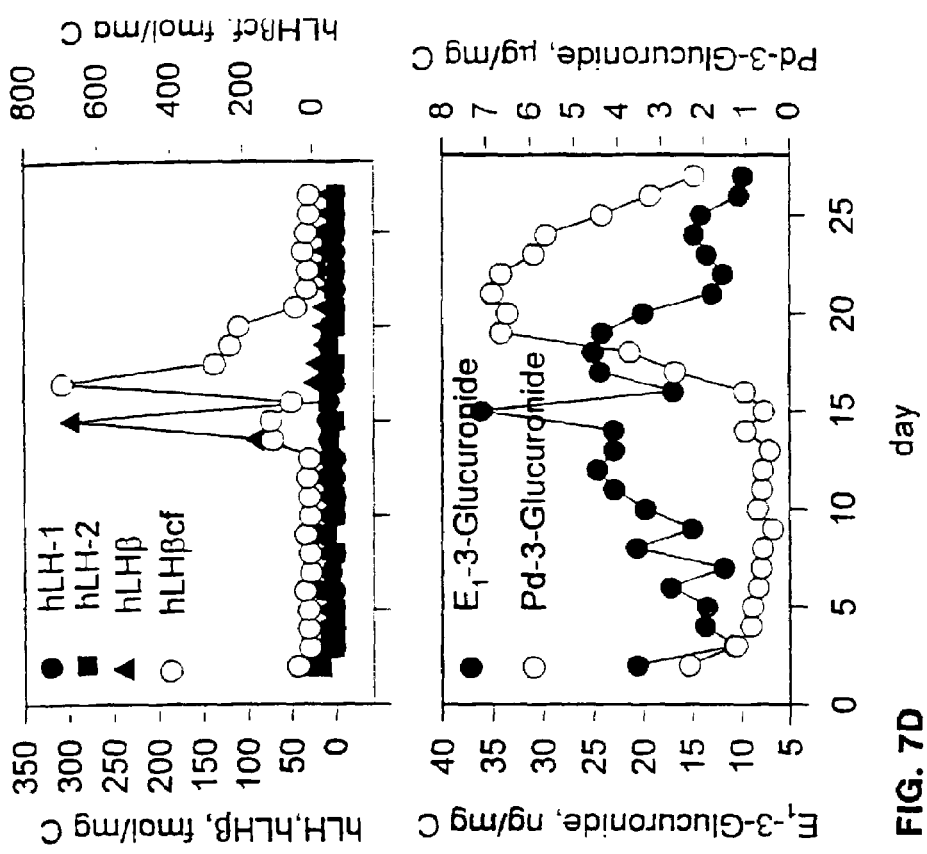

The urinary hLH molecular forms profile in two subjects (patient #75-3, patient #67-5) who did not express measurable intact hLH in either of the hLH assays (FIGS. 7A and 7C respectively). Both hLH free β subunit and hLHβcf surges are clearly apparent. FIGS. 7B and 7D illustrate the corresponding urinary steroid metabolite patterns for the cycles. It can be inferred from the steroid profiles that the subjects experienced normal ovulatory cycles, even in the absence of detectable intact hLH. Concentrations were normalized to creatinine. Day 1 is the first day of menses.

FIG. 8.

Box plot of urinary hormone values for postmenopausal women. The box extends to the 25th and 75th percentile. The upper and lower bars indicate the 90th and 10th percentile respectively. The upper and lower symbols indicate 95 and 5 percentile points respectively. The solid line inside the box marks the value of the 50th percentile. The dashed line represents the mean of concentration (n=107). The wide range of Y values necessitated use of a log scale.

FIGS. 9A–9B.

Urinary hormone profile of a patient obtained using monoclonal antibody based IRMAs (FIG. 9A) and RIA using polyclonal antibodies (provided by NIDDKD) to hLH and hLHβ (FIG. 9B). Concentrations were normalized to creatinine. Day 0 is the day of the hLH surge.

FIG. 10.

Binding of hLH and hLHβ specific antisera (NIDDKD) with hLHβcf in RIA format.

Figure 11A:
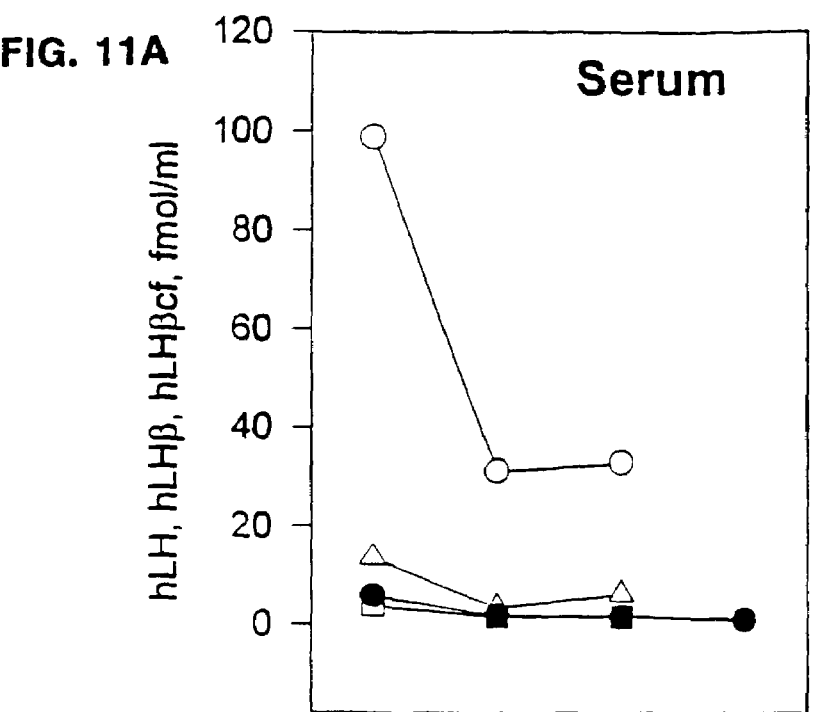
Figure 11B:
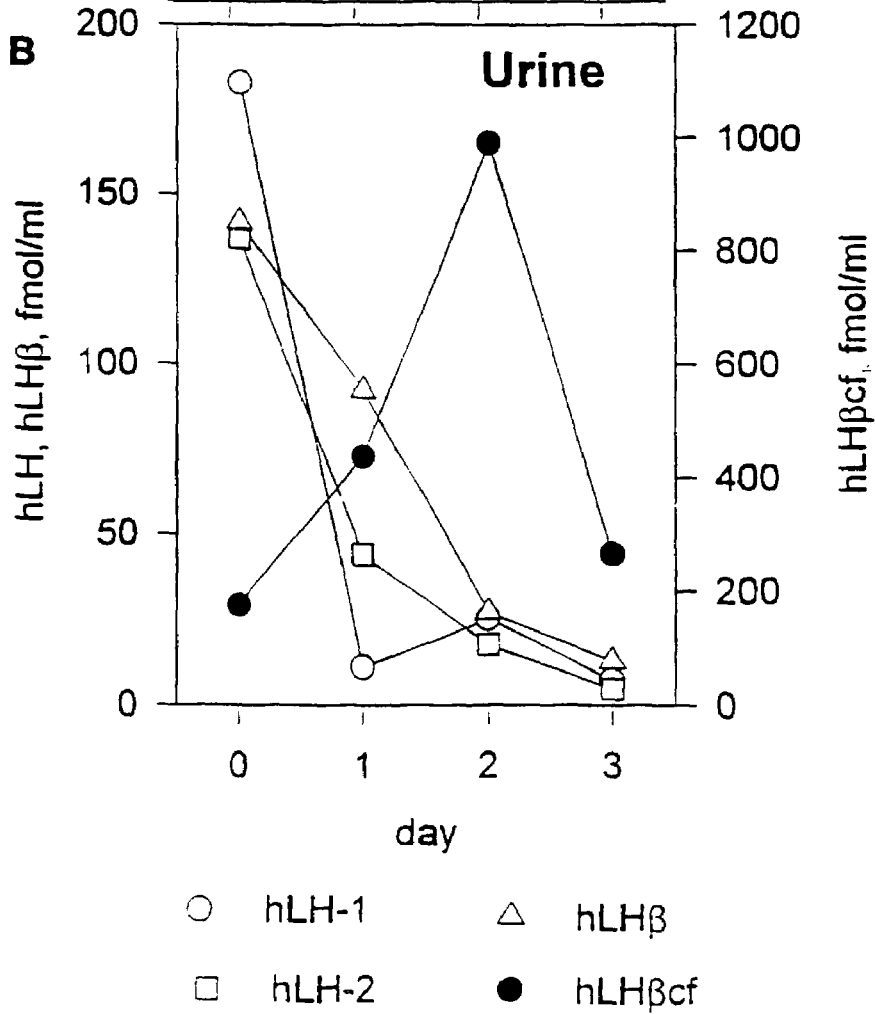

FIGS 11A–11B.

hLH and hLHβcf in serum and urine of the same patient. The blood levels of intact hLH (open circles) and hLHβcf (closed circles) are illustrated in FIG. 11A. Only a small amount of the hLHβcf was detected in the blood. FIG. 11B illustrates the urinary values for hLH and hLHβcf in the urine for the same days of collection. The surge of hLH (day 0) and the surge of hLHβcf (1–2 days later) were detected in urine, but the peak of hLHβcf lags behind that of the intact hLH by 1–2 days, suggesting that the origin of urinary hLHβcf is a consequence of the peripheral or renal metabolic processing of intact hLH.

FIGS. 12A–12C.

Profile of woman JD classified as perimenopausal and analyzed by the hLHβcf urinary assay. Consecutive first morning void urines were collected. The first day of collection was at random and not correlated to first day of menses as the ten day collections. Both patient JD and patient MJU (see FIG. 13) were over 45 yrs old but were having regular menstrual cycles. Both women have two LH surges and two ovulations as shown by the middle pattern of steroids. The women were followed over time. Patient JD who displayed a clear postmenopausal-like pattern of hLHβcf concentration in urine, began to experience irregular cycles within six months of this collection and became postmenopausal within two years.

FIGS. 13A–13C.

Patient MJU was classified as perimenopausal. FIG. 13A shows the hLHβcf pattern observed in first morning void urines collected in 1991. This pattern is similar to that observed for premenopausal women. MJU is still not postmenopausal at the present time but is experiencing irregular cycles. Conventional urinary measurements of hLH by the Delfia assay did not show differences between patient JD (see FIG. 12) and patient MJU while the hLHβcf assay of the present invention correctly predicted that JD was closer (exhibited temporal proximity) to menopause despite having regular cycles at the time of urine collection. Additional patients exhibited similar profiles.

FIGS. 14A–14F.

Figure 14A:
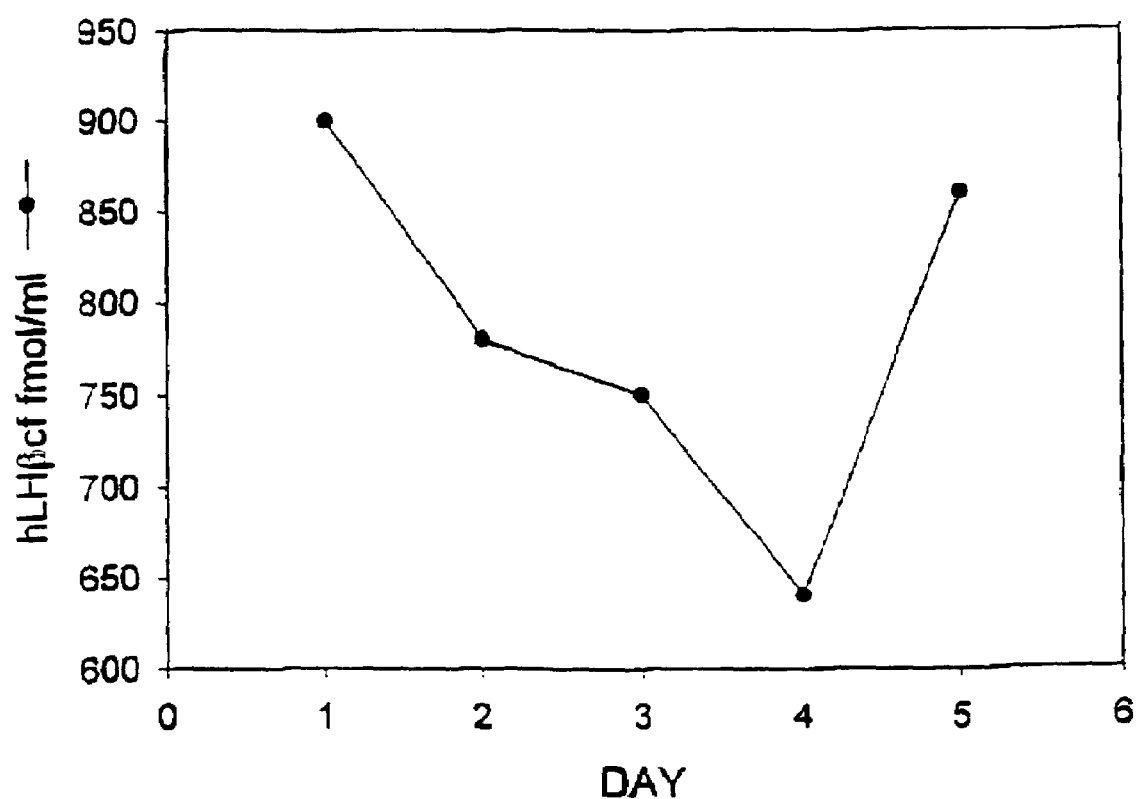
Figure 14B:
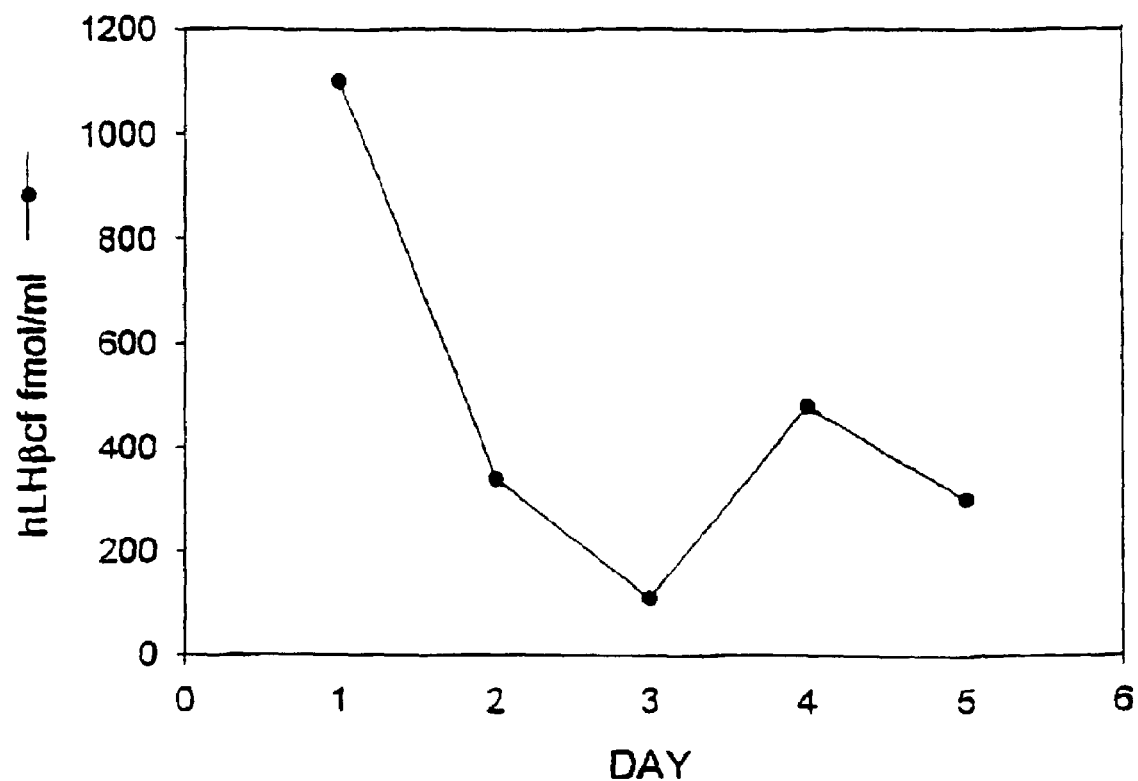
Figure 14C:
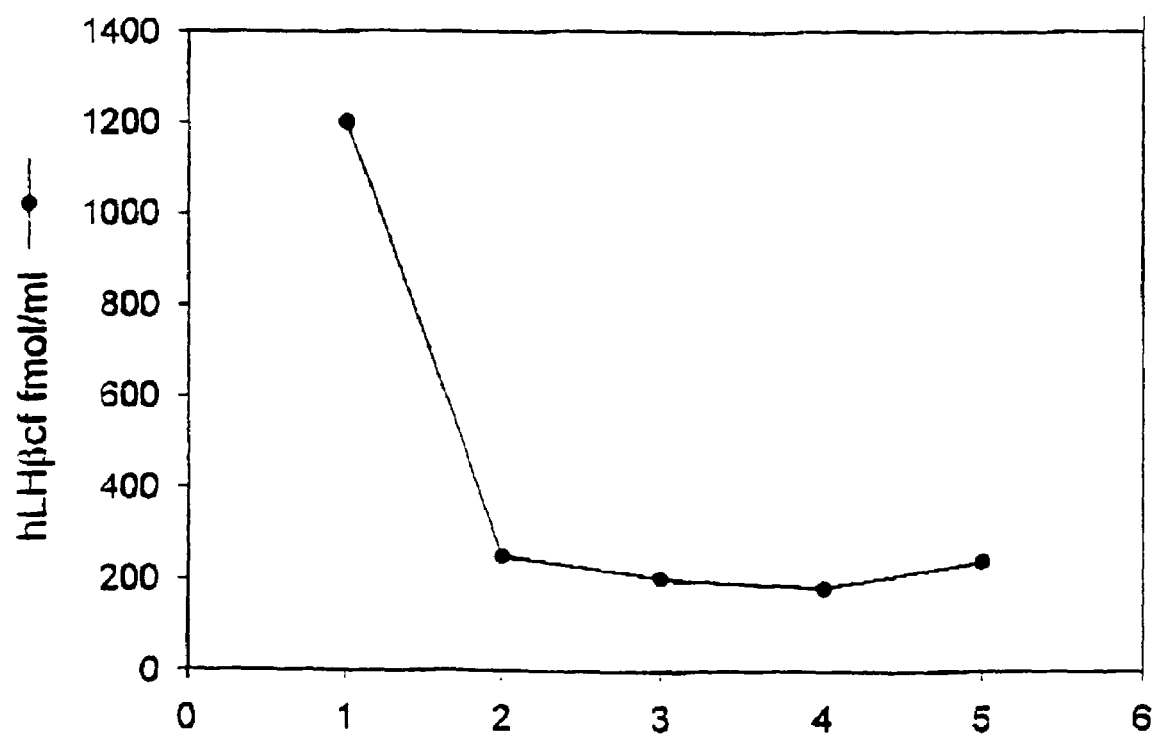
Figure 14D:
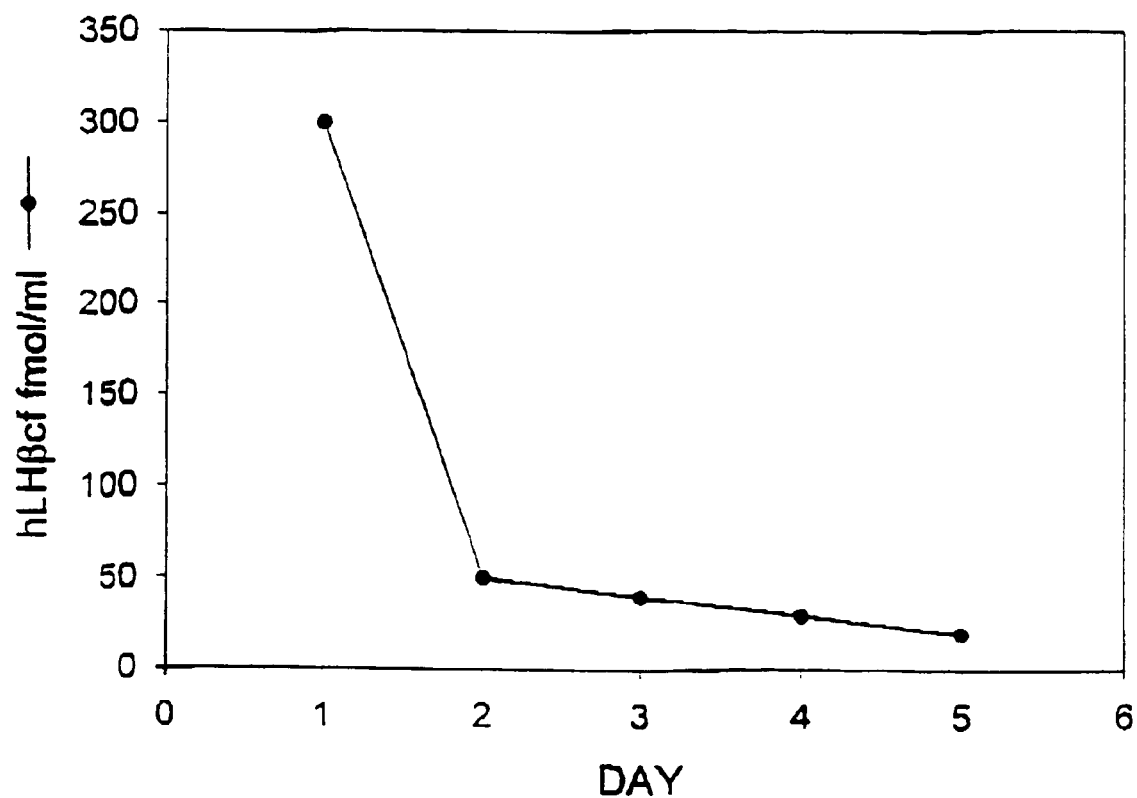
Figure 14E:
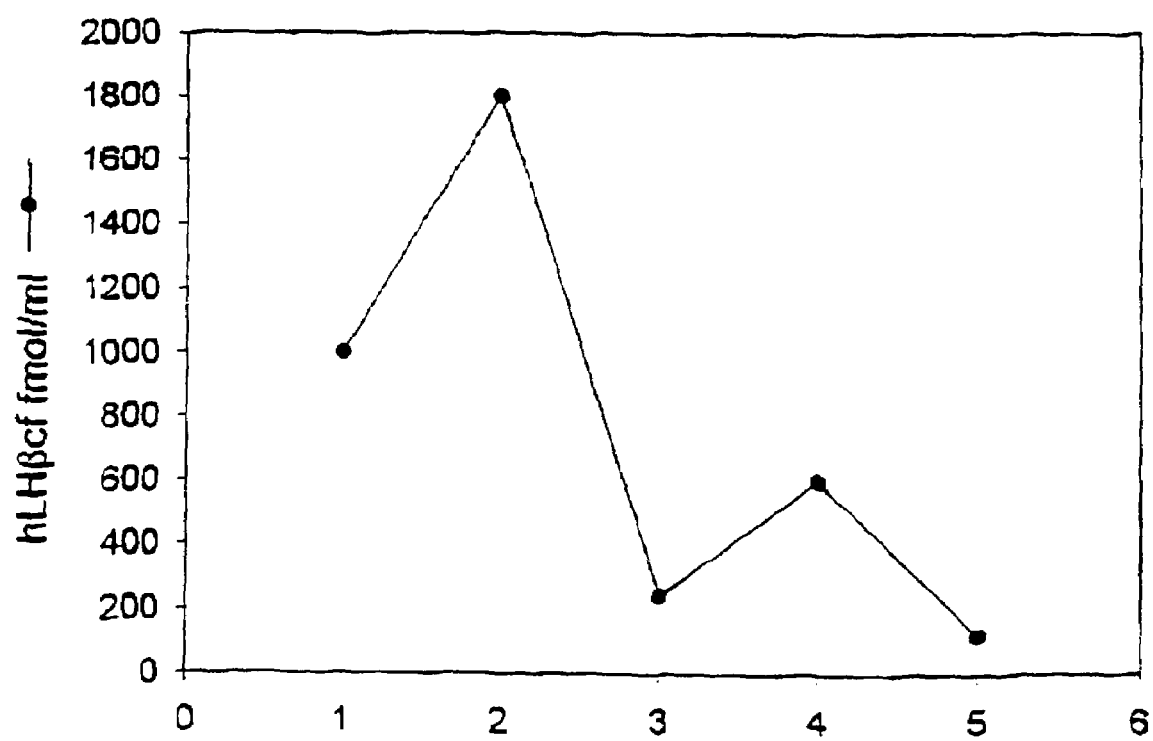
Figure 14F:
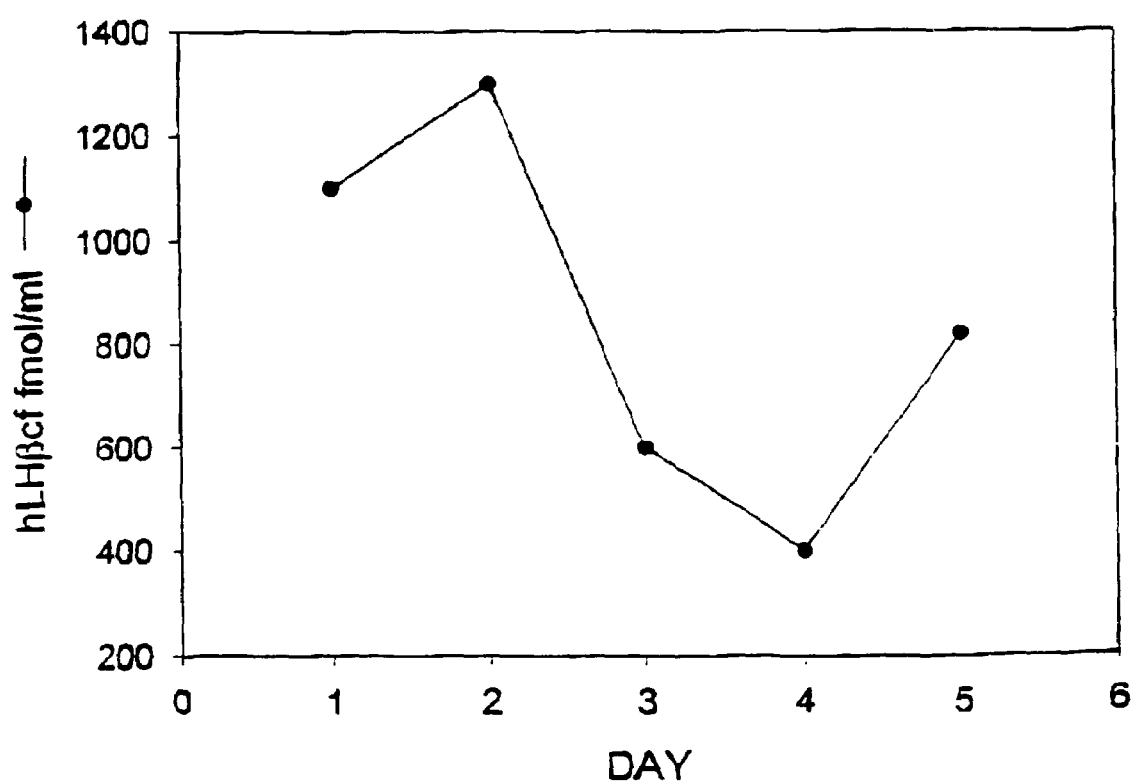

Measurements of the concentration of hLHβcf in the first morning void urine of three women before Estrogen replacement therapy (ERT) (FIGS. 14A, 14C, 14E) and after ERT (FIGS. 14B, 14D, 14F). The area under the curve was calculated and is indicated. The profile for patient LK displays an area under the curve of 3050 before ERT and 1650 after ERT (FIGS. 14A–14B). The profile for patient VP displays an area under the curve of 1350 before ERT and 280 after ERT (FIGS. 14C–14D). The profile for patient NP displays an area under the curve of 3200 before ERT and 3260 after ERT (FIGS. 14E–14F).

DETAILED DESCRIPTION OF THE INVENTION

This invention provides a method for predicting onset of menopause for a female subject by determining the amount of hLHβcf or hLHβcf-related molecule in a sample comprising (a) contacting the sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for known postmenopausal female subject(s) or (ii) the amount determined for known premenopausal female subject(s), wherein amounts of hLHβcf or hLHβcf-related molecule in the sample similar to amounts of hLHβcf or hLHβcf-related molecule in the known postmenopausal samples indicates temporal proximity to onset of menopause, amounts of hLHβcf or hLHβcf-related molecule in the sample similar to amounts of hLHβcf or hLHβcf-related molecule in the known premenopausal samples indicates temporal distance to onset of menopause for the subject.

In an embodiment of this invention step (a) comprises contacting the sample with an antibody which specifically binds a region of hLHβcf comprising a carbohydrate moeity under conditions permitting formation of a complex between the antibody and hLHβcf. In one embodiment of this invention, the antibody is B152.

In another embodiment of this invention, step (a) further comprises another antibody which specifically binds to hLHβcf without substantially cross-reacting with the antibody, hLH, hLHβ or hCGβcf under conditions permitting formation of a complex between the antibody and hLHβcf.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

This invention also provides a method for predicting onset of menopause for a female subject by determining the amount of hLHβcf or hLHβcf-related molecule in a urinary sample comprising (a) contacting a capturing antibody which specifically binds to hLHβcf without substantially cross-reacting with hLH, hLHβ or hCGβcf with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with an antibody which specifically binds to hLHβcf without cross reacting with hLH, hLHβ or hCGβcf under conditions permitting binding of antibody and antigen in the sample; (e) measuring the amount of bound antibody on the bound matrix, thereby determining the amount of hLHB or hLHβcf-related molecule in the sample; and (f) comparing the amount of hLHβcf or hLHβcf-related molecule in the sample determined in step (e) with either (i) the amount determined for known postmenopausal female subject(s) or (ii) the amount determined for known premenopausal female subject(s), wherein amounts of hLHβcf or hLHβcf-related molecule in the sample similar to amounts of hLHβcf or hLHβcf-related molecule in the known postmenopausal samples indicates temporal proximity to onset of menopause, amounts of hLHβcf or hLHβcf-related molecule in the sample similar to amounts of hLHβcf or hLHβcf-related molecule in the known premenopausal samples indicates temporal distance to onset of menopause for the subject.

In an embodiment of this invention step (a) comprises contacting the sample with an antibody which specifically binds a region of hLHβcf comprising a carbohydrate moeity under conditions permitting formation of a complex between the antibody and hLHβcf. In one embodiment of this invention, the antibody is B152.

In one embodiment of this invention, step (f) further comprises another antibody which specifically binds to hLHβcf without substantially cross-reacting with the antibody, hLH, hLHβ or hCGβcf under conditions permitting formation of a complex between the antibody and hLHβcf. According to one embodiment, this invention further comprises (a) removing of the sample from the matrix; and (b) washing the bound matrix with an appropriate buffer.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

This invention further provides a method for determining the onset of menopause of a female subject comprising (a) obtaining samples from the female subject; and (b) determining the amount of hLHβcf or hLHβcf-related molecule in the samples, the stable presence of elevated levels of basal hLHβcf indicating onset of menopause in the subject.

According to one embodiment of this invention, step (b) comprises (a) contacting the sample with an antibody which specifically binds to hLHβcf without substantially cross-reacting with hLH, hLHβ, or hCGβcf under conditions permitting formation of complex between the antibody and hLHβcf; (b) measuring the amount of the complex, thereby determining the amount of hLHβcf or hLHβcf-related molecule in the samples; and (c) comparing the amount of hLHβcf or hLHβcf-related molecule in the sample determined in step (b) with either (i) the amount determined for known postmenopausal female subject(s) or (ii) the amount determined for known premenopausal female subject(s), the stable presence of elevated levels of basal hLHβcf indicating onset of menopause in the subject.

In one embodiment of this invention, step (a) further comprises another antibody which specifically binds to hLHβcf without substantially cross-reacting with the antibody, hLH, hLHβ or hCGβcf under conditions permitting formation of a complex between the antibody and hLHβcf.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

This invention additionally provides a method for assessing ovarian function in a subject by determining the amount of hLHβcf or hLHβcf-related molecule in a sample comprising (a) contacting the sample with an antibody which specifically binds to hLHβcf without substantially cross-reacting with hLH, hLHβ or hCGβcf under condition permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for subject(s) with normal ovarian function or (ii) the amount determined for subject(s) with abnormal ovarian function, wherein amounts of hLHβcf or hLHβcf-related molecule in the sample similar to amounts of hLHβcf or hLHβcf-related molecule in the samples from subjects having normal ovarian function indicates normal ovarian function, amounts of hLHβcf or hLHβcf-related molecule in the sample similar to amounts of hLHβcf or hLHβcf-related molecule in the samples from subjects having abnormal ovarian function indicates abnormal ovarian function for the subject.

According to one embodiment of this invention, step (a) further comprises another antibody which specifically binds to hLHβcf without substantially cross-reacting with the antibody, hLH, hLHβ or hCGβcf under conditions permitting formation of a complex between the antibody and hLHβcf. In an embodiment of this invention, the abnormal ovarian function is hyperactivity. In another embodiment of this invention, the abnormal ovarian function is hypoactivity.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

In addition, this invention provides a method for determining the efficacy of hormone replacement therapy in a subject by determining the amount of hLHβcf or hLHβcf-related molecule in a sample comprising (a) contacting a sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for pre-treatment sample(s) or (ii) the amount determined for prior treatment sample(s) or (iii) the amount determined for known pre-menopausal sample(s) or (iv) the amount determined for known postmenopausal sample(s), wherein changes in the amount of hLHβcf or hLHβcf-related molecule in the sample indicates efficacy of the hormone replacement therapy for the subject; amounts of hLHβcf or hLHβcf-related molecule in the sample similar to amounts of hLHβcf or hLHβcf-related molecule in the known premenopausal samples indicates efficacy of the hormone replacement therapy for the subject; amounts of hLHβcf or hLHβcf-related molecule in the sample similar to amounts of hLHβcf or hLHβcf-related molecule in the known postmenopausal samples indicates lack of efficacy of the hormone replacement therapy for the subject.

According to an embodiment of this invention, step (a) further comprises another antibody which specifically binds to hLHβcf without substantially cross-reacting with the antibody, hLH, hLHβ or hCGβcf under conditions permitting formation of a complex between the antibody and hLHβcf. In an embodiment of this invention, the hormone is estrogen.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

Further, this invention provides a method of predicting pregnancy outcome in a subject by determining the amount of hLHβcf or hLHβcf-related molecule in a sample comprising (a) contacting a sample with an antibody which specifically binds to hLHβcf without substantially cross-reacting with hLH, hLHβ or hCGβcf under conditions permitting formation of a complex between the antibody and hLHβcf; (b) measuring the amount of complexes formed, thereby determining the amount of hLHβcf or hLHβcf-related molecule in the sample; and (c) comparing the amount of hLHβcf or hLHβcf-related molecule in the sample determined in step (b) with either (i) the amount determined for pregnant subject(s) or (ii) the amount determined for non-pregnant subject(s), wherein amounts of hLHβcf or hLHβcf-related molecule in the sample similar to amounts of hLHβcf or hLHβcf-related molecule in the pregnant samples indicates a positive outcome, amounts of hLHβcf or hLHβcf-related molecule in the non-pregnant samples indicates a negative outcome of pregnancy for the subject.

In one embodiment of this invention, the sample is a urinary sample, a first morning void urine sample, an aggregate sample of the first morning void urine samples for at least two consecutive days or an aggregate sample of the first morning void urine samples for five or more consecutive days. In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

Finally, this invention provides a diagnostic kit for determining the onset of menopause for a female subject comprising (a) an antibody which specifically binds to hLHβcf without substantially cross-reacting with hLH, hLHβ or hCGβcf; (b) a solid matrix to which the antibody is bound; and (c) reagents permitting the formation of a complex between the antibody and a sample.

According to one embodiment, this invention further comprises control sample(s) selected from the group consisting of premenopausal sample(s),. perimenopausal sample(s), postmenopausal sample(s) and male sample(s).

In an embodiment of this invention, the antibody is labeled with a detectable marker. In one embodiment of this invention, the detectable marker is a radioactive isotope, enzyme, dye, magnetic bead, or biotin. In one embodiment of this invention, the radioactive isotope is $I^{125}$.

A monoclonal antibody, B-505, is produced by the hybridoma cell designated ATCC accession No. HB-12000. This hybridoma cell line was deposited on Dec. 11, 1995 with the American Type Culture Collection (ATCC), 12301 Parklawn Drive, Rockville, Md. 20852, U.S., under the provision of the Budapest Treaty for the International Recognition of the Deposit of Microorganism for the Purpose of Patent Procedure.

hLH beta core fragment (hLHβcf), isolated from human pituitaries is homologous to the hCG beta core fragment (hCGβcf), and may be a marker of normal pregnancy, Down's syndrome, and certain cancers. Antibodies to the hLHβcf, have been developed which are applied in sensitive assays including immunoradiometric assays for urinary measurements. One of the antibodies recognizes an epitope on the hLHβcf, which is not present on the hCGβcf, hLH, or hLHβ. This specific hLHβcf antibody acts cooperatively with other newly-developed antibodies to produce an assay with a sensitivity of 1 fmol/ml of hLHβcf. This specificity makes it possible to measure hLHβcf in urine in the presence of hLH, hLH beta, or the hCGβcf. Although the hLHβcf used to develop specific antibodies was purified from pituitaries, the assays developed recognize this metabolite in urine. Measurements of heterodimeric hLH as compared to hLHβcf in the urine of cycling women indicated that the concentration of hLHβcf rose as high as 6–7 times the concentration of hLH starting a day after the midcycle surge. The novel measuring systems described herein allow the precise quantitation of this hLH metabolite in urine.

Three groups of women were analyzed: young cycling premenopausal, perimenopausal (as defined by current clinical and age-related criteria), and postmenopausal women. The appearance of the hLHβcf in the urine of all three groups of women was pulsatile on a daily basis when measured in first morning void urine specimens. This was unexpected since hLH was pulsatile on an hourly basis in blood. Both the pattern of pulsatility and the amplitude of the pulses differed between young cycling women and postmenopausal women. Statistical analyses indicated that the wide range of differences between postmenopausal and premenopausal women made it possible to discriminate among the three groups of women. Postmenopausal women can be sampled for any ten day interval while cycling women can be sampled during the follicular phase. Data indicates drastically different qualitative and quantitative patterns of premenopausal and perimenopausal patients closest to menopause. Perimenopausal women displayed postmenopausal patterns in many cases. Women with premature ovarian failure exhibited a pattern similar to that seen for postmenopausal women, but with a distinguishing higher levels of hLH metabolite. Treatment of women with GnRH agonist peptide appeared to expel the hLH β core fragment directly from the pituitary. This demonstrates potentially two origins of this molecular form of hLH, both directly from the pituitary and from breakdown of circulating hLH in the kidney or other peripheral tissue compartments. A chromatographic technique was developed to separate the hLHβ core fragment generated in the pituitary from that which usually appears in the urine of postmenopausal women.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Predicting Onset of Menopause Using a Urinary hLH B Core Fragment Assay

Measuring hLH β Core Fragment In Urine. Although immunological evidence indicated the presence of a β subunit fragment of hLH in the urine of postmenopausal women, no direct evidence that the molecules came from hLH and not from hCG was available until now (Iles, et al., 1992; Kovalevskaya, et al., 1995; Neven, et al., 1993). The presence of this approximately 10,000 M.W. molecule was apparent on gel filtration chromatography and presented a background threshold problem in the application of assays for the hCG β core fragment as a potential cancer marker in postmenopausal women (O'Connor, et al. 1994; Iles, et al., 1992; Birken, et al., 1993; Kovalevskaya, et al., 1995; Neven, et al., 1993). The specific measurement system for such a fragment from hLH differentiates it from the homologous fragment from hCG β which is known to be present at high levels in the urine of pregnant women and in patients with hCG-secreting cancers including a variety of cancers of the reproductive system (O'Connor, et al. 1994; Stenman, et al., 1993 ;de Medeiros, and Norman, 1991; Birken, et al., 1993; Kovalevskaya, et al., 1995; Lee, et al., 1991; Krichevsky, et al., 1991). Using pituitary tissue extracts as starting material, an hLH β core fragment whose structure appears in FIG. 1 was successfully isolated. The specific measuring systems for the hLH β core fragment can be used in the presence of the hCG β core fragment as well as in the presence of hLH (Kovalevskaya, et al., 1995). The hLH β core fragment assay can measure 1.3 fmol/ml of this epitope and cross-reacts only 1% with hLH β core fragment and less than 1% with hCG β core fragment. A MALDI-TOF delayed extraction reflector mass spectrometer has been employed to visualize the sizes of the hCG and hLH β core fragments which are both broad peaks of 9500–10000 AMU. It has been possible to measure the size of the urinary form of the hLH β core fragment (also 10K in a partially purified preparation).

The β fragment of hLH from human pituitaries (see, FIG. 1, Seq. ID. No.:1) has been isolated and sensitive and specific two-site assays to this molecule have been developed (Birken, et al., 1993; Kovalevskaya, et al., 1995). The hLH β core fragment is homologous to the hCG fragment. The hLH β core fragment, isolated from a pituitary extract and its structure is slightly heterogeneous and is composed of residues 6–40 linked to 49–93 or 55–93 (Birken, et al., 1993). The hLH β core fragment is clearly detected in postmenopausal urine at high concentrations using antibodies to the similar metabolite of hCG (Iles, et al., 1992; Neven, et al., 1993). The hLHβcf epitope in urine is highly stable as is the hCG metabolite making it a very useful urinary marker. Subunit dissociation is not a problem with stable markers.

A very important characteristic of useful urinary assays is stability of the analyte. The hLHβcf is exhibits a stable profile, making it far superior to the use of heterodimeric hormones. Parent hLH tends to dissociate, especially in urine. The stability of both the pituitary and the urinary forms of the hLHβcf is illustrated in Table I.

TABLE I

| | Storage Conditions for Stability Testing | | | | |
|---|---|---|---|---|---|
| Molecular Form | −80 C | 29 days, 4 C | 29 days, 22 C | 1 day, 37 C | 40 freeze/ thaws |
| Pit. hLHβcf | 153 +/− 7.6 | 162 +/− 7.8 | 163 +/− 7.8 | 183 +/− 2.4 | 155 +/− 5.6 |
| Urinary hLHβcf | 243 +/− 34 | 199 +/− 11 | 203 +/− 13 | 290 +/− 7.7 | 211 +/− 21 | values expressed as means at concentrations of fmol/ml +/− 1SD

Figure 2:
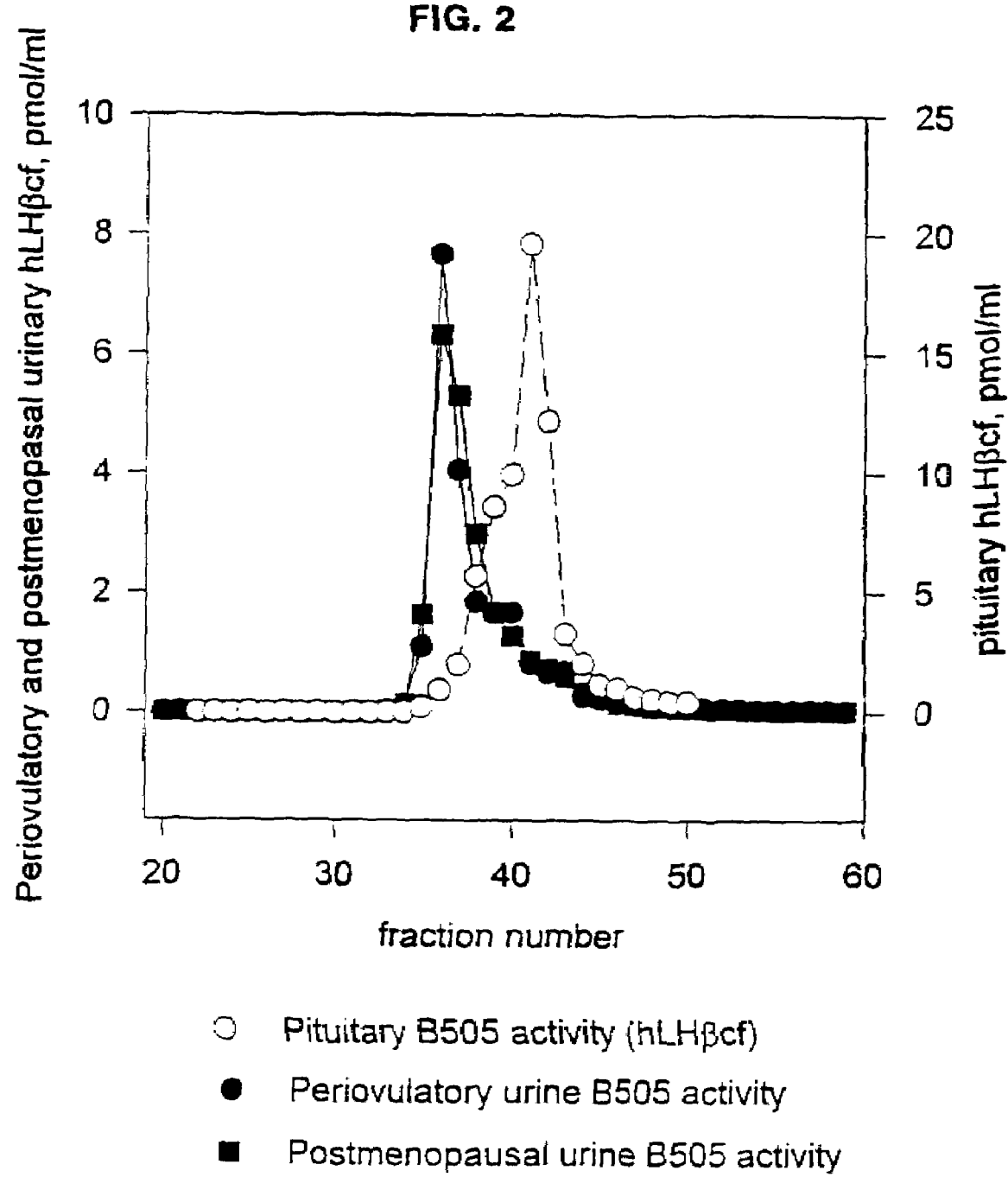

In the urine of a normally cycling woman, hLHβcf appears starting with the LH surge and peaking generally 1–3 days after the urinary LH surge peak concentration. The urinary hLHβcf appears at concentrations 2–10 times that of hLH on a molar basis. Chromatographic separatory data based on different elution times on reverse phase high pressure liquid chromatography (HPLC) indicates that the urinary and pituitary forms of the hLHβcf differ. This difference may be within the carbohydrate moieties (see FIG. 2). The hCG β core fragment is known to contain sugar moieties trimmed down to their mannose cores while the pituitary hLH β core fragment appears to contain sulfate and resemble the structure of hLH in carbohydrate. An antibody, designated, B152, raised against a choriocarcinoma-derived, nicked hCG, binds to a carbohydrate moiety of hCG and cross reacts with hLH, hLH free beta and hLH beta core. The size of the urinary form on mass spectrometry resembles that of the pituitary homolog (10K). The urinary form of hLHβcf may have trimmed carbohydrate.

Although antibodies were developed to the pituitary form of the hLH β core fragment, the antibodies react with great sensitivity to the 10,000 M.W. fragment which is present in the urine of postmenopausal women. This fragment elutes with a midpoint of fraction 65 on the gel filtration profile of a postmenopausal urine concentrate on Superdex 200. The hLHβcf from both a human pituitary extract and postmenopausal urine would both appear at high concentration in the identical area of fraction 65.

Studies of a series of normal ovulatory cycles indicated that the measurement of the hLHβcf in urine is much easier than the hLH surge in urine because of: (1) the high concentration of fragment, (2) its stability, and (3) some monoclonal antibodies do not recognize all forms of hLH and can miss the hLH surge. The instability of hLH is illustrated by the daily urine profile of a normal cycling woman whose urine contains on detectable heterodimeric hLH but only hLHβ and hLHβcf. Studies of several ovulatory cycles shows that the hLH β core fragment is present at all times at a basal pattern level but at concentrations more than an order of magnitude lower than the hLHβcf found in the urine of postmenopausal women (see FIGS. 3A–3K). This also illustrates paradigm of first morning void studies from day 1 of menses to day 10. While both premenopausal and postmenopausal women exhibit daily first morning urine hLHβcf concentrations in a pulsatile fashion, the concentrations are so dramatically different that summing areas under the peaks define non-overlapping area values allowing statistical differentiation of the two populations.

Daily first morning void urine specimens from peri menopausal and postmenopausal women for 60 consecutive days were measured urinary hLH with the Delfia kit system as well as steroids and creatinine and validated the serum Delfia kit for urine measurements using added glycerol as a stabilizer for heterodimeric hLH (Saketos, et al., 1994). Several complete cycles from premenopausal women and a number of ten day first morning voids from postmenopausal women and follicular phase ten day collections from premenopausal women were also collected. Statistical analyses of these patterns were conducted by determining the area under the peak for a ten day interval and then performing least squares analysis of variance with pair-wise post hoc comparisons. Statistically significant differences, after Bonferroni correction was found for premenopausal/postmenopausal comparisons. Power analyses for this study, which consisted of ten consecutive first morning void urines, menstrual days 1–10 for premenopausal and perimenopausal women, required log-transformed values. The test populations consisted of 13 premenopausal women, four perimenopausal and eight postmenopausal.

Figure 4:
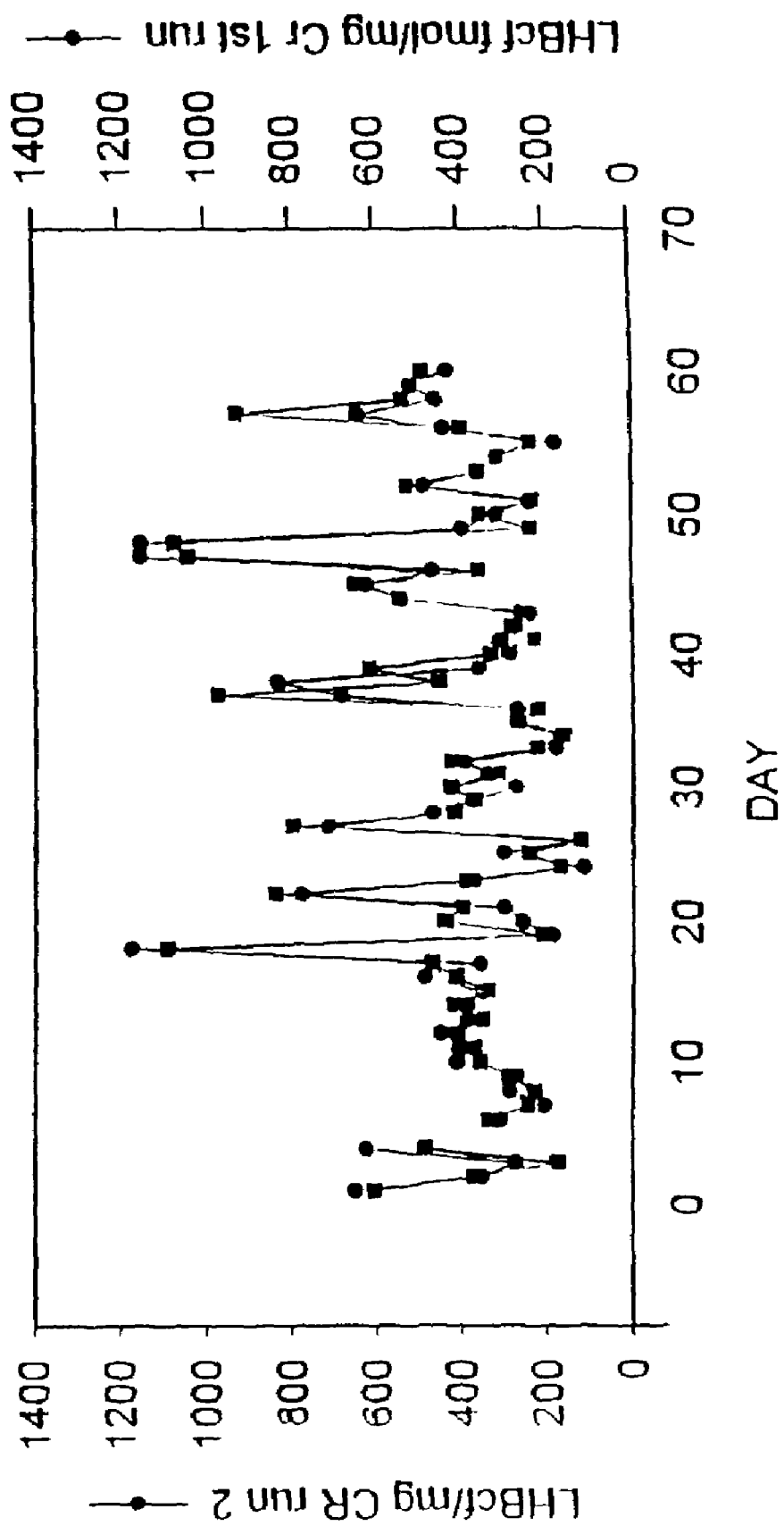

A 60 day random collection of first morning void urine from a postmenopausal woman was assayed (see FIG. 4). The assay was repeated twice on the same samples weeks later after freeze thaws. The identical pulsatile pattern with the same concentrations was observed.

Expression of Urinary hLHβcf. A cohort of women was studied (n=15). A peak of hLHβcf was observed to occur over a 3–4 day period, commencing on the day of hLH surge and reaching a maximum value of 560 (SE 119) fmo/mg creatinine at 1–3 days post urinary intact hLH peak (see FIG. 5). A peak of hLH free beta subunit (hLHβ) was observed to occur simultaneously with that of the intact molecule. Although the levels of hLHβ approximately those of the intact hormone, the levels of hLHβcf were several fold higher (see FIG. 5).

A surge of hCGβcf immunoreactivity peaked two days post intact hLH, generally coincident with the peak of hLHβcf but at levels which were 100 fold less than those for hLHβcf. Since the cross-reaction of the hCGβcf immunoassay with the pituitary hLHβcf was determined to be 1–2%, and that the true cross-reactivity with the urinary form is unknown, it may be that the total signal detected in the hCGβcf assay is in fact due to cross-reaction with hLHβcf (Birken et al. 1996).

The urinary hLH surge was detected by A407-B207 (hLH-1) antibody configuration. Eight of the 15 cycles were rerun in a different antibody configuration assay B406-A201 (hLH-2). These assays were constructed using monoclonal antibodies to different hLH epitopes (See Table III). Both hLH-1 and hLH-2 assays gave the same day of hLH surge, but the concentration of hLH in two assays differed significantly (paired t-test, P=0.0005).

This observation further illustrates that the levels of hormone detected immunologically in urine reflect the differential conservation (or stability) of hLH epitopes excreted into urine and caution that monoclonal antibodies may be too specific to provide an accurate estimation of the level of all forms of hLH in either blood or urine (Pettersson et al., 1991; Pettersson et al., 1992; Martin-Du-Pan et al., 1994; Costagliola et al., 1994; Mitchell et al., 1995; Barbe et al., 1995 Pettersson and Soderholm, 1991).

Figure 6:
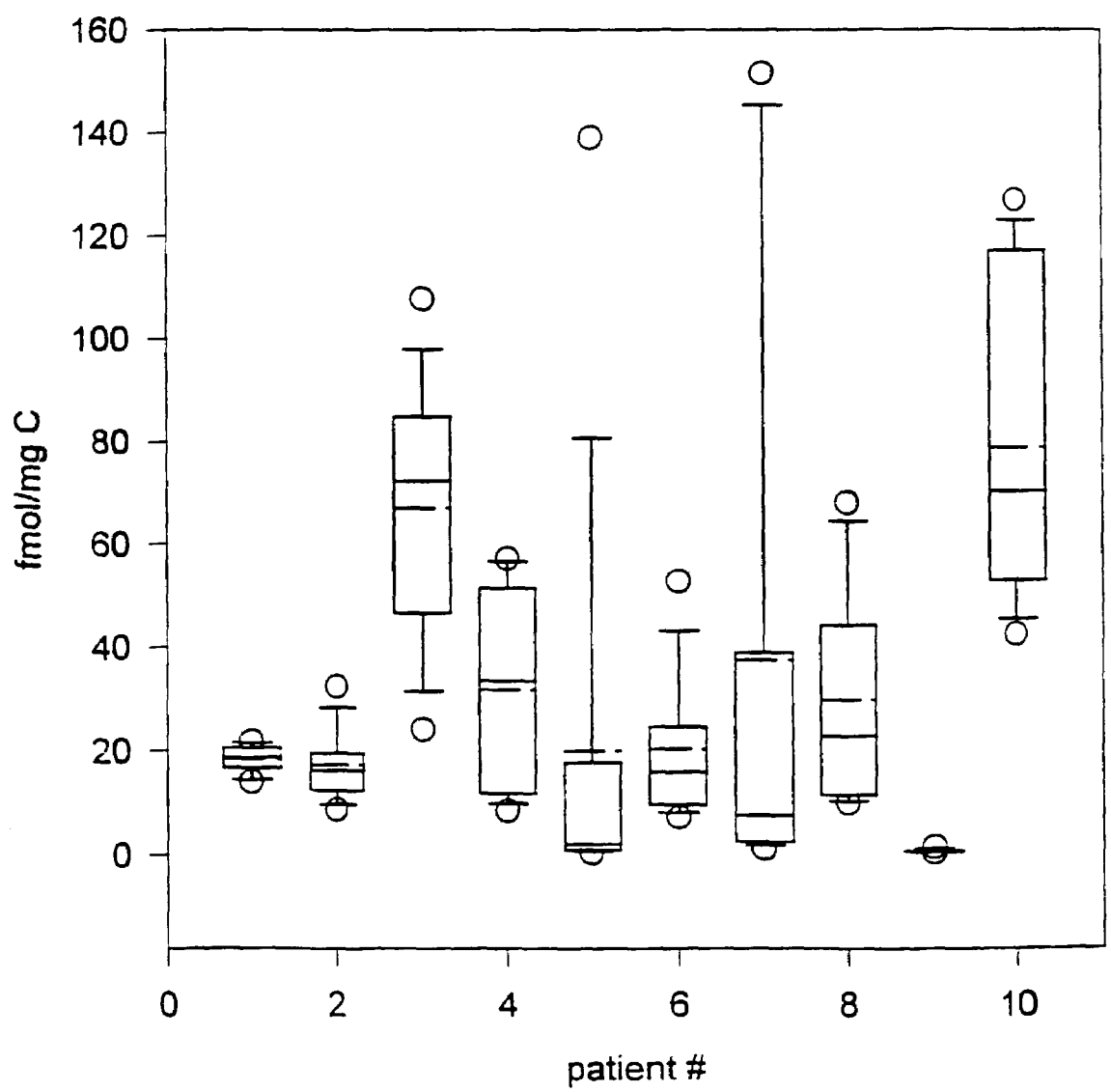

All cycles were characterized by irregular pulsations of hLHβcf. The basal level of hLHβcf in ten patients during first of the follicular phase (100 samples) was 32 (SE 4) fmo/mg creatinine, with a wide range of concentrations, reflecting the spikes of hLH occurring before the periovulatory surge of hLHβcf (FIG. 6).

Examination of daily first morning urines from four women in which the hLH assays, indicated that ovulation occurred as judged by the inversion of the urinary estrogen/progesterone metabolite ratio (Baird et al., 1991). Data from two of the four women are presented in (FIG. 7). Evidence from the urinary steroids that ovulation occurred suggested that one or more of the following occurred. The intact hormone may have been completely cleared by an alternative pathway. The intact hormone may have dissociated completely into subunits or been totally degraded into fragments prior to excretion. Alternatively, the antibodies used in these measurements, which were raised to the pituitary form of hLH, may have failed to recognize the urinary isoform of hLH present in the sample. That the lack of evidence for intact hLH was not a consequence of these subjects producing an isoform of hLH peak was found in other cycles tested from these subjects.

These cycles were characterized by the presence of a periovulatory peak of hLHβcf within the expected time interval. These results suggest that an assay incorporating the detection of all three urinary analytes would provide the most sensitive detection of periovulatory hLH. However, although hLHB is most often observed to peak coincident with the intact molecule (FIG. 5), it appears that it can occasionally occur one day earlier (Kovalevskaya et al., 1995). On the other hand, hLHβcf, usually peaked 1–3 days later than the intact molecule (FIG. 5) and this midcycle peak of hLHβcf has been detected in all four cycles in which there was undetectable intact hLH in the urine (FIG. 7).

The levels of intact hLH, hLHβ, hLHβcf, and hCGβcf were evaluated in a total of 107 healthy postmenopausal women (FIG. 8). The mean concentration of hLHβcf for the 107 postmenopausal women was 236 (SE 35) fmol/mg creatinine.

Urines collected from eleven normal males (age 20–60) yield a value of 41 (SE 13) fmol/mg creatinine (See Table II).

TABLE II

Concentration of hLHβcf in Urine

| | Periovulatory urine, basal level | Periovulatory urine, surge | Post-menopausal urine | Male urine |
|---|---|---|---|---|
| Mean +/− SE, fmol/mg C | 32 +/− 4 | 560 +/− 119 | 236 +/− 35 | 41 +/− 13 |
| Size | 100* | 15 | 107 | 11 |

SE - standard error of mean; fmol/mg
C - concentration of hLHβcf normalized per mg creatinine;
* - days 1 to 10 from 10 women.

hLH and hLHβ were measured in urine using IRMA's incorporating specific monoclonal antibodies (FIG. 9A) and by RIA (FIG. 9B), using polyclonal antisera directed against either intact hLH or hLHβ, supplied by the National Hormone and Pituitary Program, NIDDKD. The RIA reagents were designed for serum assays and indicate a single day pre-ovulatory elevation of both hLH and occasionally hLHβ in blood.

When these same reagents are employed for hLH or hLHβ measurement in urine however, a broad peak for either hormone was obtained. These observations can be explained by the presence of hLHβcf in the urine (FIG. 9A). When FIGS. 9A and 9B are compared, it is apparent that the day of maximum hLHβ by IRMA is different from the RIA value, probably due to the greater cross-reactivity of the hLHβ polyclonal antiserum to hLHβcf.

Figure 10:
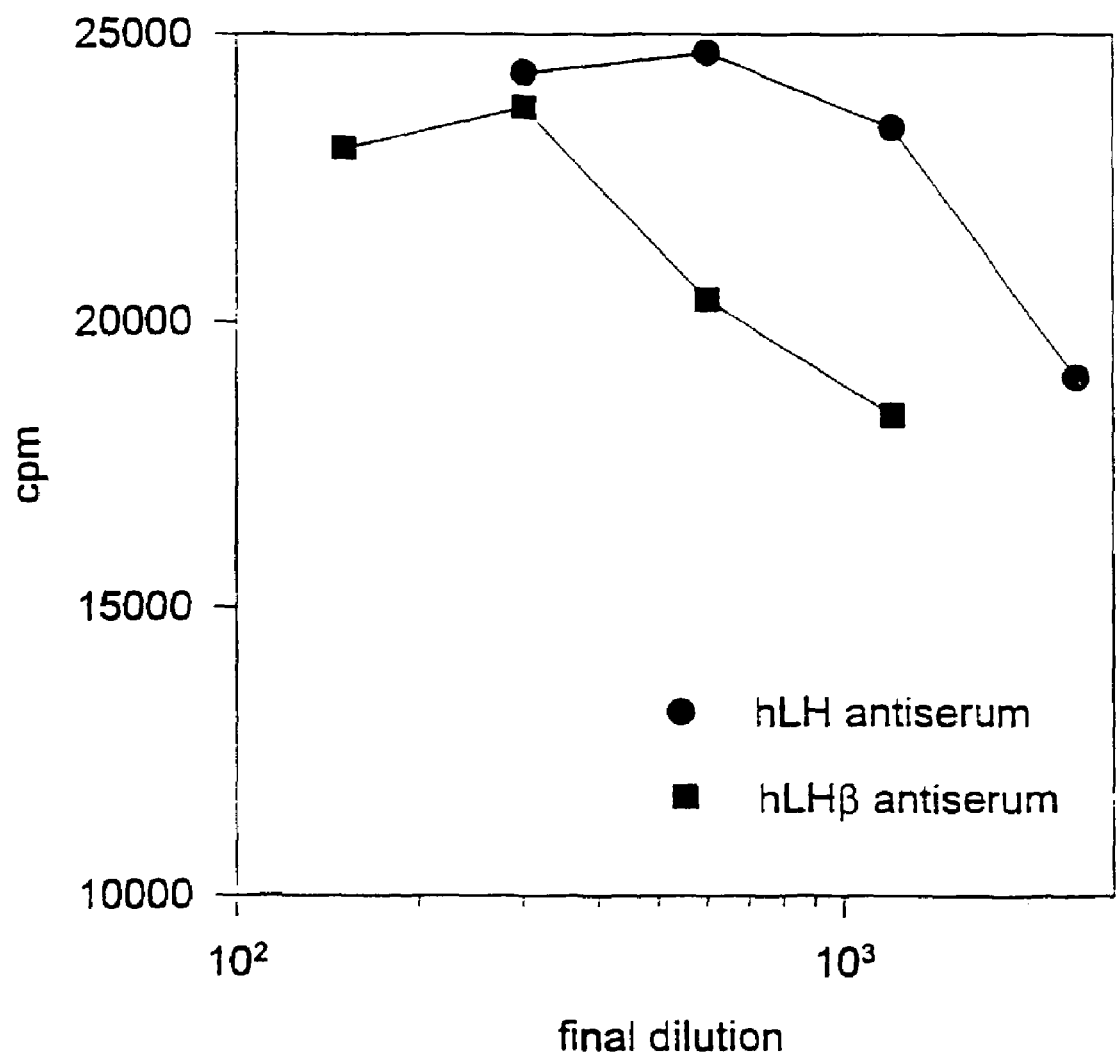

The cross-reactivities of the polyclonal antisera to hLHβ and to intact hLH with hLHβcf were further evaluated in an RIA using hLHβcf labeled with $I^{125}$ (FIG. 10). Both polyclonal antisera clearly recognized hLHβcf. The pituitary form of hLHβcf was used in this experiment but a similar reactivity pattern should also be observed with the urinary variant of this molecule, since the monoclonal antibodies developed to the pituitary material all appear to share epitopes present on the urinary molecule.

A comparison of the concentration of hLHβcf in blood and urine was undertaken by collecting paired samples beginning on the first day of the hLH surge in urine (detected by "First Response" kit) and continuing for three subsequent days in a single subject. The collection was repeated during a subsequent cycle. FIG. 11 illustrates corresponding values in blood and urine for hLH, hLHβ and hLHβcf. The hLH-1 assay provided a significantly stronger signal in serum than did the hLH-2 assay. The hLHβ signal appears synchronously with the intact peak in this subject in urine. However, the hLHβ surge starts to grow and is detected only in the urine.

The basal level (i.e. follicular level) of hLHβcf in normally cycling women was similar to the level which was detected for male urine (see Table II). Both of these groups differ markedly from the values obtained for postmenopausal subjects which were characterized both by much higher levels and a wider range of values (FIG. 8). Levels of intact hLH were low in these subjects in both assays for hLH, but there was a substantial quantity of hLHβ, perhaps reflecting dissociation of the intact molecule. Only low values of hCGβcf were detected.

There was no significant hLHβcf surge in blood but a substantial hLHβcf surge in urine, indicating that urinary hLHβcf is a product of hLH metabolic processing. The lag time in the appearance of the fragment suggests that it may be a consequence of metabolic processing by the kidney or in some other compartment.

Two assays were used for intact hLH measurements (hLH-1 and hLH-2. The hLH-2 assay was highly specific for the intact hLH molecule, but occasionally produced a weak signal in urinary assays. The hLH-1 assay, although less specific for hLH, (some crossreactivity with hCG, (see Table III) but could detect signals of greater amplitutde, and had better detection when applied to urine specimens. The hLH-2 assay barely detected hLH in the serum of this subject but detected the urinary form as well as the hLH-1 assay, which performed equally well in both serum and urine. This probably reflects metabolic processing of the hLH which affects epitope presentation upon passage of blood to urine.

TABLE III

Assay Specificity and Sensitivity

| Antigen | hLH-1 | hLH-2 | hLHβ | hLHβcf | hCGβcf |
|---|---|---|---|---|---|
| hLH, % | 100 | 100 | 29 | 1 | <1 |
| hLHβ, % | <1 | <1 | 100 | 1 | <1 |
| hLHβcf, % | <1 | <1 | <1 | 100 | 2 |
| hCGβcf, % | 2 | <1 | <1 | <1 | 100 |
| hCG, % | 100 | <1 | <1 | <1 | 1 |
| hCGβ, % | 31 | <1 | <1 | 1 | <1 |
| LDD*, fmol/ml | 1 | 1.5 | 1.4 | 1 | 0.6 |

LDD*—least detectable dose

Predicting Onset Of Menopause In Perimenopausal Women. A urinary-based assay was used which measures a highly stable metabolite of luteinizing hormone which appears in the urine of all individuals but displays different daily patterns of excretion in relation to the physiological state of the individual. The immunoassays to measure the hLH beta core fragment were developed to the form of the fragment isolated from the pituitary and described above. These assays also measure the form of the molecule that appears in urine (Burger, et al., 1995). The hLHβcf is elevated in normal premenopausal women one or two days after the mid-cycle LH surge (Burger, et al., 1995). The present invention is based on measurements during the follicular phase, usually the ten day period between day one of menses and day 10. Five to ten days of daily, first morning void urine specimens were collected, starting at day one or day two of menses. The amount of hLHβcf concentration in fmole/ml was measured and normalized to creatinine (divided by creatinine concentration in mg/ml). It was determined that premenopausal patterns are easily distinguishable from postmenopausal patterns based on the simple algorithm of area under the peak when at least 5 daily measurement are performed. The average area under the peak for premenopausal women is usually 2–3 standard deviations away from the area under the peak of postmenopausal women (their urine sampling is for 5–10 days, first morning void, at random since they do not have menstrual cycles). The test population of interest is perimenopausal women. The perimenopausal women examined exhibited a hLHβcf profile similar to the profile for premenopausal women or a hLHβcf profile similar to the profile for postmenopausal women. Two perimenopausal women with postmenopausal patterns were known to enter menopause within a year of analysis while two women showing premenopausal patterns did not enter menopause for several years. Several women were followed for a period of years.

Figure 12A:
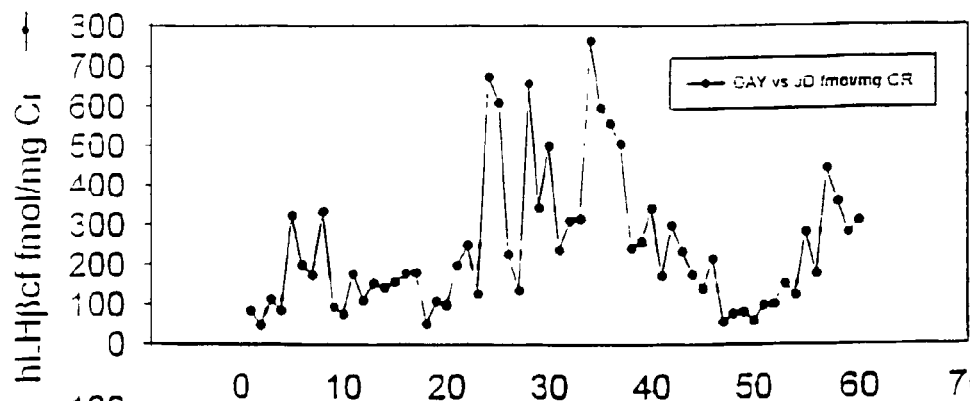
Figure 12B:
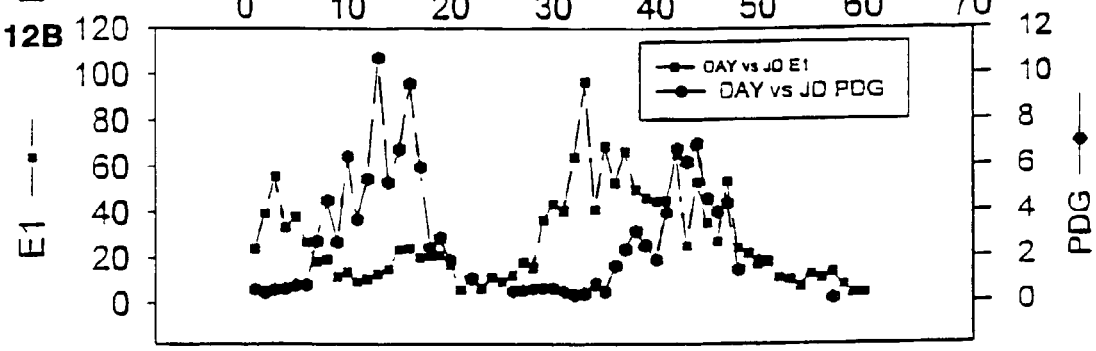
Figure 12C:
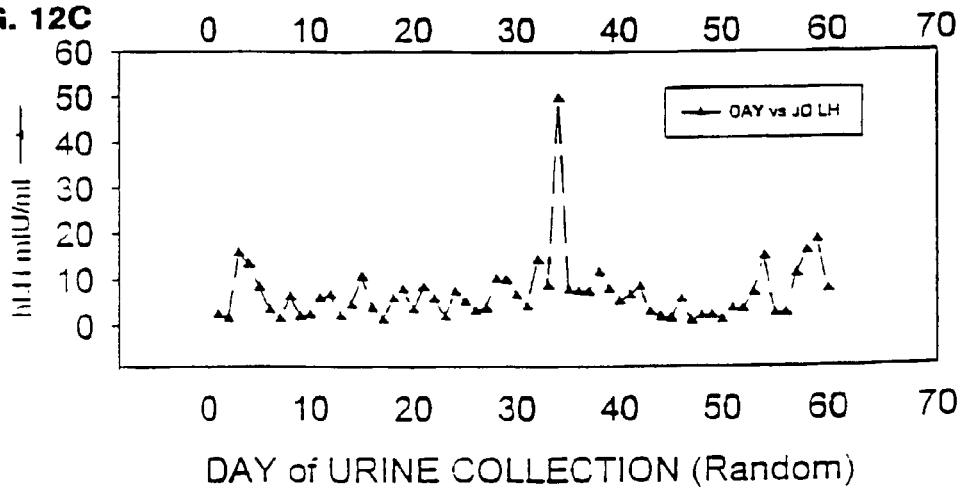
Figure 13A:
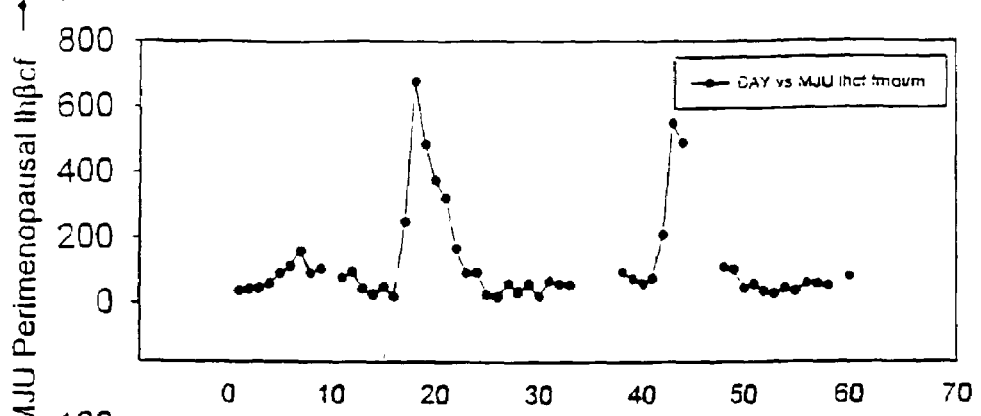
Figure 13B:
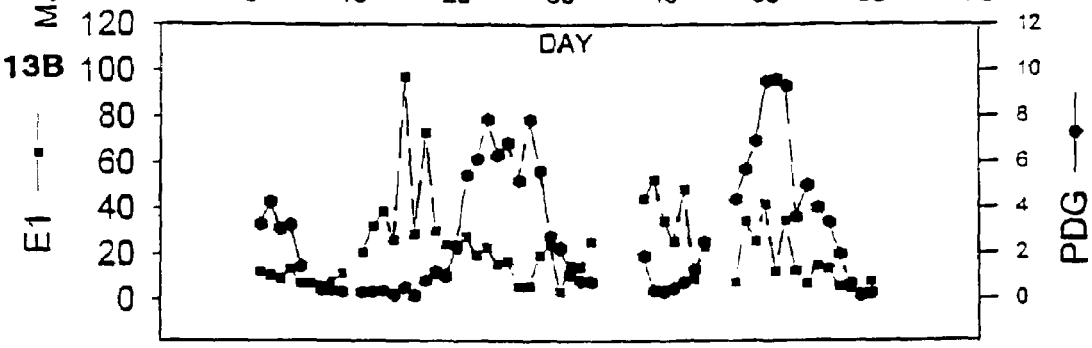
Figure 13C:
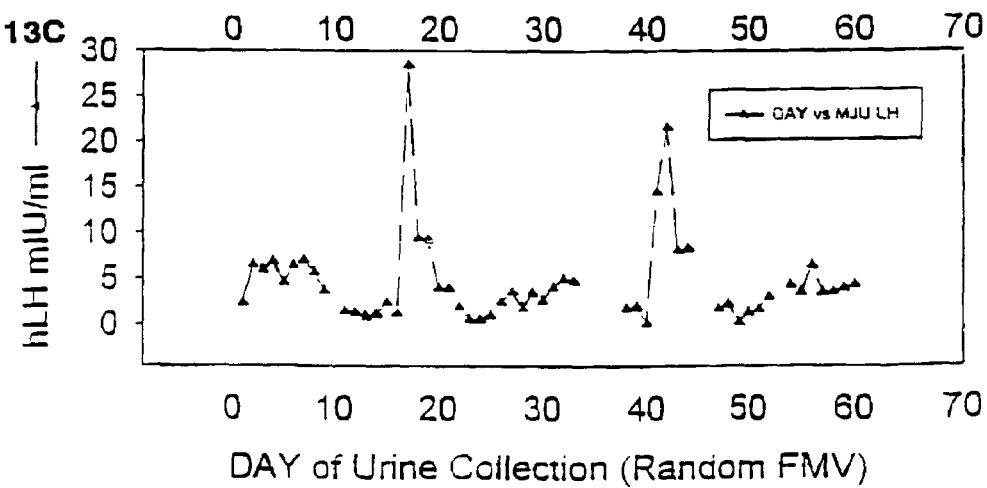

The discrimination of the urinary hLHβcf assay is shown in FIGS. 12–13. These are patients whose urines were collected for 60 days as described above. Both patients were considered to be perimenopausal but both had normal regular cycles. The hLHβcf profile of patient JD is similar to the profile of postmenopausal women while the profile of patient MJU is similar to the premenopausal profile. The assay correctly predicted which patient was closer (exhibited temporal proximity) to menopause since JD, who is now postmenopausal, began to experience irregular cycles within a year of this collection, while MJU only began to experience such irregularities, several years later than JD. JD became postmenopausal within two years.

Predicting Onset of Menopause in Perimenopausal Subjects Using the Area Under The Curve Determined for hLHβcf. This experiment takes advantage of the excellent and unique assay described in detail above. The hLHβ subunit, hLHβcf, which is analogous to the hCG beta core fragment in structure and by its similar appearance chiefly in urine. The assay, described in detail above, is a two-site immunoassay to the core fragment molecule which is sensitive to less than 1 fmole/ml in urine. The hLHβcf molecule appears in urine at concentrations much higher than that of hLH 1–2 days after the LH surge in normal premenopausal women. In postmenopausal women, the urinary hLHβcf appears in a pulsatile fashion when consecutive first morning void urines are examined. The amplitutude of the fluctuations in postmenopausal individuals are much greater than during the follicular phase of premenopausal individuals forming the basic design of a differentiating assay. Simply summing the area under the peak of graphs plotting day of collection versus hLHβcf in fmoles/mg Creatinine results in sets of numbers that easily distinguish premenopausal from postmenopausal subjects (see Table IV). The Lhβcf urine samples should preferably be at least 2 ml of first morning void urine. The data in Table IV suggests that in the perimenopausal group, the two subjects reflecting areas greater than 3,000 exhibit the greatest temporal proximity to menopause. In other words, of the patients presented in this experiment, the two subjects with areas greater than 3,000 are closest to menopause. Interestingly, they are still experiencing menstrual cycles; one exhibits regular cycling. The subject with an area of 344 is predicted to be temporally distant from menopause.

In this experiment, the perimenopausal group was defined by age. Women 43 years or older were included in this group if they were not already menopausal. Samples were taken from this group during the follicular phase for ten days where day 1 was mensus. Samples taken from the menopausal group were from any ten days. Samples were taken from the premenopausal group during the follicular phase for ten days where day 1 was mensus.

Interestingly, for these data, the mean Area value for the premenopausal group (n=13) is 237, while the mean value for the postmenopausal group (n=8) is 2267.5, a value nearly 10-fold increased as compared with the premenopausal group. Of the six perimenopausal samples, two Area values (3095 and 3735) exceed the mean Area value for the postmenopausal group; one (344) is less than twice the mean Area value for the premenopausal group; two (614 and 684) are between two and three times the mean Area value for the premenopausal group; and one (849) is between three and four times the mean Area value for the premenopausal group.

Of course, mean Area value is not the only measure or method of analysis of the data, in order to determine similarity of a perimenopausal sample with the premenopausal or postmenopausal groups. Median values are also important, as is regression analysis, pattern analysis and multiplex analyses.

TABLE IV

Area under the Curve for hLHβcf Determined in Samples Taken from Subjects

| Premenopause | Perimenopause | Postmenopause |
|---|---|---|
| 190 | 344 | 2764 |
| 53 | 3095 | 4597 |
| 613 | 684 | 2501 |
| 321 | 614 | 2070 |
| 148 | 849 | 1688 |
| 73 | 3735 | 1168 |
| 251 | | 2181 |

TABLE IV-continued

Area under the Curve for hLHβcf Determined in Samples Taken from Subjects

| Premenopause | Perimenopause | Postmenopause |
|---|---|---|
| 378 | | 1171 |
| 6 | | |
| 129 | | |
| 603 | | |
| 165 | | |
| 158 | | |

Predicting onset of menopause in perimenopausal subjects using subject-described symptoms and the area under the curve determined for hLHβcf. In this experiment, a questionnaire was used to asses if women had regular cycles and if they thought they had menopause symptoms. In this experiment, the "menopause symptoms" was the subject's subjective answer which may not truly indicate menopause symptoms. Additionally, self-defined menopause symptoms may vary from subject to subject. Further, accurate description of symptoms may result, not from onset of menopause, but from other unidentified causes.

"Cycles" indicate the presence of regular menstrual cycles as described by the subject. This should be an objective measure of a change, though not necessarily an accurate measure of menopausal status for the reasons as described above. Under the heading of "comments" prediction is: (1) far (indicating temporal distance from menopause by Area value); (2) closer (indicating approaching or increasing temporal proximity to menopause by Area value); (3) very close (high temporal proximity to menopause by Area value); and (4) n.c. (indicating a result that is not consistent with the Area value based on a woman's report of symptoms or cycle regularity).

Collection of urine samples from the subjects and measurements of hLHβcf were performed as described above. The data was plotted and area under the curve (Area) was calculated as described above. The data are presented together with the corresponding questionnaire data in Table V below:

TABLE V

Symptoms and Prediction of Onset of Menopause

| Patient | Age | Symptom | Regular Cycle | Area | Comment |
|---|---|---|---|---|---|
| 1 | 46 | no | yes | 737 | closer |
| 2 | 47 | yes | no | 166 | n.c. |
| 3 | 45 | no | yes | 317 | far |
| 4 | 48 | yes | yes | 26 | n.c. |
| 5 | 47 | no | yes | 48 | far |
| 6 | 45 | yes | yes | 1518 | very close |
| 7 | 46 | no | yes | 89 | far |
| 8 | 47 | no | yes | 22 | far |
| 9 | 47 | yes | no | 1518 | very close |
| 10 | 47 | no | yes | 62 | far |
| 11 | 43 | no | yes | 249 | far |
| 12 | 46 | slight | yes | 13 | far |
| 13 | 48 | yes | yes | 752 | close |
| 14 | 50 | no | yes | 866 | close |
| 15 | 43 | no | yes | 101 | far |
| 16 | 43 | yes | no | 849 | close |

Experimental Procedures

Hormones hLH(AFP-4261-A), hLHβ (AFP-3477A), anti-human LH-2 antisera and anti-human LH beta-1 antisera for RIA were provided by the National Hormone and Pituitary Program, NOTCHED. Standards used in the IRMA's were hLH (AFP-8270B), hLHβ (AFP-3282) (all from the same source). HCGβcf were prepared as described by Birken (Birken et al., 1988; Birken et al., 1993).

Iodination of hLHβcf, hLH, hLHβ, purification and iodination of monoclonal antibodies: iodination and separation of monoclonal antibodies and hormones were performed as previously described (Kovalevskaya et al., 1995).

Liquid Phase RIA with $^{125}$I-hLHβcf

The liquid phase radioimmunoassay (RIA) procedure was conducted as follows: 0.1 ml serial dilutions of rabbit antiserum to hLH or hLHβ in phosphate buffered saline (PBS) containing normal rabbit serum (Sigma) and 0.1% sodium azide were added to 0.2 ml $^{125}$I-hLHβcf (30,000 cpm) in PBS with 0.1% BSA (Sigma). The mixture was then incubated overnight at 4° C. Then 0.2 ml sheep anti-rabbit serum was added and this solution was incubated overnight at 4° C. The precipitate containing radioactive hLHβcf was separated by centrifugation and $^{125}$I-content determined by gamma counting (Packard Cobra).

Liquid Phase RIA for hLH and hLHβ

Liquid phase radioimmunoassays (RIA) were conducted as recommended in NHPP instructions. In brief, the binding buffer (buffer A) consisted of PBS supplemented with 0.1% BSA and 0.1% sodium azide. 0.1 ml hLH- or hLHβ-antiserum in PBS 1% normal rabbit serum was also added. Both antisera were prepared in rabbits. This solution was mixed with 0.1 ml of radiolabeled hLH or hLHβ (30,000–40,000 cpm) in buffer A and incubated overnight at 4° C. Then 0.2 ml of a sheep anti-rabbit serum was added and mixture was incubated overnight at 4° C. The precipitate containing bound radioactive hLHβ or hLH was separated by centrifugation and counted in a gamma counter.

IRMA

The methodology for the construction and validation of Immunometric assays has been fully described (O'Connor et al., 1988). Briefly, the specificity of the antibody pairs and their capacity for simultaneous binding to antigen are determined as follows. The analytes tested for potential cross reaction with the hLHβcf monoclonal antibodies included hCGβcf, hLH (AFP 8270B), hLH free β subunit (AFP 3282B), intact hCG (CR 127) and hCG free β subunit (CR129). The range of the β core LH standards was 3.9 to 1000 fmol/ml. The range of cross reactants encompassed 3.9 to 278000 fmol/ml, depending on the analyte.

The capture antibody was adsorbed onto the wells of microtiter plates by incubating a 20 μg/ml solution of the antibody in coating buffer (0.2 M bicarbonate, pH 9.5) overnight at 4 C. The coating antibody solution was aspirated, the plates were washed (wash solution 0.9% NaCl, 0.05% Tween 20) and blocked with a 1% solution of BSA in PBS. Following incubation with the BSA solution (minimum 3 hours at room temperature) the blocking solution was removed, the wells were again washed with wash solution and 200 ml/well of the appropriate hLHβcf standards or potential cross-reacting molecules were added in phosphate buffer B (0.05M phosphate with 0.1% bovine gamma globulin, 0.15M NaCl and 0.1% NaN$_3$). After overnight incubation at 4 C, the plates were again aspirated and washed. The 200 ml (50,000 cpm–100,000 cpm) of appropriate $^{125}$I-labeled detection antibody (listed with double asterisks in Table 2) was added to the wells which were again incubated for 24 h at 4C. The tracer was aspirated, the plates washed with water, the individual well placed in glass tubes and the radioactivity determined in a Packard Cobra gamma counter. Doses were determined by interpolation from a smoothed spline transformation of the data points.

In addition to hLHβcf assays, three other assays, described earlier, were used for hLH and hLHβ (Krichevsky et. al., 1994) and for the hCGβcf (Krichevsky et al., 1991).

For the assay of urinary hLH and its metabolic forms, the following antibody pairs were employed: For intact hLH, B406*-A201**; for the hLH free beta subunit, B408*-B409**; and for the hLHβcf B505*-B503**. Prior to assay, the urines are thawed, the pH is adjusted with 1.0M Tris (pH 9.5), 50 μl/ml urine, centrifuged and aliquoted (200 μl/well) into 96 well microtiter plates which had been previously coated with capture antibody and blocked with BSA. A serially diluted standard curve of the appropriate analyte (intact hLH, hLH free beta subunit or hLHβcf) is added in buffer B to the wells and the plate is incubated overnight at 4C. The assay is performed from that point identically to that described for antibody characterization.

Antibody Characteristics and Assay Construction

The development and validation of immunometric assays for intact hLH, hLH free beta subunit (Krichevsky et al., 1994), hLHβcf (Kovalevskaya et al., 1995) have been described previously. Briefly, microtiter wells (Immulon II, Dynatech, Chantilly Va.) were coated (200 μl/well) with the appropriate, pretitered solution of the capture antibody in sodium bicarbonate buffer (pH 9.5, 0.2M) by overnight incubation at 4° C. The coating antibody solution was then aspirated, and after blocking the plates with 1% BSA in PBS (overnight 4° C.) the plates washed 5 times with wash solution. Urine specimens, after pH adjustment to approximately 7.5 (1.0M TrisHC1, pH 9, 50 μl/ml), or standards in PBS/0.1% sodium azide/0.1% bovine IgG buffer (Buffer B) and urine controls were then applied to the wells (200 μl/well) and incubated overnight at 4° C. The wells were aspirated, washed five times with wash solution and the appropriate radioiodinated detection antibody (tracer)(50,000 cpm–100,000 cpm in buffer B) was added to the wells (200 μl/well). After an additional overnight incubation at 4° C., the wells were aspirated, the plates washed with deionized water 5 times and the wells were separated and counted in a gamma counter (Packard Cobra). Values for the samples and controls were interpolated from a smoothed spline transformation of the standard curve.

hLH was measured by A407 (capture)-B207 (tracer) (hLH-1 assay) and B406-A201 (hLH-2) (Krichevsky et al., 1994). HLHβ was measured by the B408-B409 assay (Krichevsky et al., 1994) hLHβcf was detected by the B505-B503 assay (Kovalevskaya et al., 1995) and hCGβcf- by the B210–B108 assay (Krichevsky et al., 1991). The sensitivities of assays (least detectable dose, LDD) were calculated as plus two standard deviations (SD) of the standard 'zero'.

For hLHβcf, hCGcf, hLHβ, hLH-1 and hLH-2, intraassay coefficients of variation were 9%, 4%, 6%, 13% and 10% respectively. Interassay coefficients of variation were 9%, 10%, 15%, 21% and 10% for hLHβ, hCGβcf, hLGB, hLH-1 and hLH-2 respectively.

Sample Collection

A) First morning void urine (FMV): Specimens were collected from normally cycling women, ranging in age from 20 to 42 years. The specimens were stored in the subject's home freezer until delivered to the laboratory.

B) Large scale periovulatory urine collection: Five subjects were provided with a home ovulation detection kit ("First Response", Carter Wallace, Inc.). Starting with the first day of a positive hLH test signal, daily 24 hour urine collections were made for the succeeding seven days.

C) Cycles without a detectable urinary intact hLH signal: Four subjects were selected from a population of women who recruited as normal controls for an investigation of hormone metabolism in premenstrual syndrome subjects. They were between the ages of 18–40 years, and were not pregnant or planning pregnancy. They had regular menstrual cycles and were not using any medication, drug or vitamin known to perturb the menstrual cycle.

D) Male urine (FMV): First morning void male urine was collected from 11 subjects between the ages of 18–60.

E) Postmenopausal urine, large volume collection: Postmenopausal urine was collected from one subject (age 66) by pooling daily collection urine for 40 days. 500 ml of this pool was processed in the same manner as the periovulatory urine pool.

F) Postmenopausal urine random collection: Postmenopausal urine was collected from 107 subjects enrolled in a study of baseline CA-125 levels in postmenopausal women (Westhoff et al., 1992). The women were recruited from patients at a general medical clinic or a screening mammography appointment. No woman was enrolled who was receiving treatment for any gynecological condition. The subjects ranged in age from 43 to 74 years.

G) Matched blood and urine collection: Matched blood and urine were obtained at the same time from a single person on two occasions, starting with the first day of a positive hLH test signal in urine according to "First Respone" kit and continuing for a total of four days.

Characterization of Urinary hLHβcf

Aliquots of the morning urine from ovulating women were assayed for hLHβcf and collections of the sequential 24 hour urines for days which tested positive were pooled, the pH adjusted to 7.5 using 1.0M Tris HC1 and sodium azide (0.1%) was added. One half of this pool was filtered through a 0.45μ membrane (Nalgene, Rochester, N.Y.) and concentrated in an Amicon Cell using a YM-3 membrane (Amicon, Danvers, Mass.). The concentrate was desalted and delpidated on a Sephadex G-15 column (Pharmacia, Piscataway, N.J.). The eluate was lyophilized and dissolved in 0.1M ammonium bicarbonate buffer, and half of it was gel filtered on double tandem colums of superose 12 (Pharmacia). The entire amount was used in the case of postmenopausal urine.

Column fractions containing hLHβcf immunoreactivity were pooled, lyophilized and then dissolved in 4M guanidine HC1 containing 0.1% TFA (pH4). This solution (1.2 ml) was applied to a Vydac C-4 Column (22×4.6 cm). A binary linear gradinet was run. Solution A was 0.1% TFA in water, Solution B was 0.1% TFA in acetonitrile. The flow rate was 1.0 ml/min; gradient 10 min 10% B to 70 min 40% B.

Pituitary hLHβcf was chromatographed under the same conditions as the urinary concentrates.

Urinary Steroid Metabolite Assays

The solid phase microtiter plate-based ELISA's for estrone-3-glucuronide ($E_1$-3-G) and pregnanediol-3-glucuronide (Pd-3-G) were performed with monoclonal antibodies provided by Carter Wallace, Inc. The enzyme-conjugated steroids were provided by Dr. Bill Lasley, and the assays performed according to the procedure of Munro et al., 1991).

hLHβcf Stability

Midcycle urine, encompassing the hLH urinary metabolite peaks, was collected from five subjects, pooled; pH was adjusted to 7.5 using 1.0M Tris HC1 and sodium azide (0.1%) added. Aliquots of the urinary midcycle peak (endogenous urinary hLHβcf) and blank urine (B105 immunoextracted to remove hCG- and hLH-associated urinary metabolites from the urine and thus reduce the background) were stored at −80° C. (control samples). Replicate samples (plus blank) were stored at 4° C., 22° C., and 37° C. for extended time periods. After each time period the samples were returned to the −80° C. freezer. The freeze/thaw specimens were removed from the −80° C. freezer from one to five times/day and thawed either at room temperature or in a water bath at ambient temperature. After the indicated number of freeze/thaw cycles the samples were returned to the −80° C. freezer. At the completion of the stability study, all of the specimens were analyzed in the same assay, in order to avoid interassay variation.

The B105 immunoextracted urine exhibited the same blank value as buffer B.

Statistical Analysis

Data were analyzed using the SigmatStat Program, version 1.01 (Jandel Corporation, San Rafael, Calif.). One-way analysis of variance with Bonferroni adjustment was used to evaluate stability studies. A comparison with a P-value less than 0.05 was considered significant.

Creatinine

Creatinine determinations were performed in a 96-well microtiter plate format by a procedure adapted from Taussky (Taussky, 1954).

Mass-spectrometry

Mass-spectrometry was performed on a Perceptive Biosystems Voyager DE RP instrument run in linear mode using a matrix of sinapinic acid or DHB.

Sialic Acid and Sulfate Analysis

Sialic acid and sulfate analysis were performed using a Bionex PAD as described (Birken et al., 1996).

Example 2

Assessing Hormone Replacement Therapy (HRT).

Clinicians caring for women must make judgements as to the ovarian state of the patient without a clear guide for classification of the patient as pre, peri or postmenopausal. Currently, decisions about estrogen replacement therapy (ERT) are usually made in response to the patient's symptoms (hot flashes, mood disorders, etc.) and chronological age rather than any objective diagnostic tests (Burger, et al., 1995; Burger, 1994a; Burger, 1994b; Hee, et al. 1993). Supplementing estradiol on an unknown background (single tests) may be hazardous to the patient. It may promote a cancer or lead to uterine hyperplasia. Detailed menstrual histories are probably the best current criteria of perimenopause (Burger, 1996;. Burger, 1994b; Metcalf, 1988; Metcalf, et al. 1981b). It is possible that the patient's symptoms are associated with other underlying problems which may be overlooked if they are attributed to early menopause. The high cost and inconvenience of multiple venipunctures for a complete serum estrogen or serum LH profile of a menstrual cycle is prohibitive as a diagnostic route. There are no good markers of the effectiveness of the doses used in estrogen replacement therapy. New markers of menopause are needed for a variety because: it may not be clear that the woman is estrogen of reasons. Symptoms may be associated with another existing disorder. Currently, serum gonadotropins, as well as serum inhibins are markers of limited use. In addition, it is not possible to perform complete LH and FSH serum assays along with urinary steroids for one or two cycles for definitive staging of perimenopause. Further, gametogenic failure precedes estrogen failure by several years and has no good chemical marker. Also, monitoring estrogen therapy would benefit from the discovery of new markers of the effectiveness of the therapy.

A test, described herein was devised which is performed using the same daily measurements of hLH beta core fragment as described above for postmenopausal women, specifically, five consecutive days of first morning void urine were collected. Using three blinded patients who received various doses of estrogen, it was determined that one woman exhibited a hLHβcf profile similar to the profile for premenopausal women. One woman exhibited a hLHβcf profile similar to the profile for postmenopausal woman and one was intermediate. This may be interpretted as meaning that one woman was not getting an adequate estrogen dose, since she remained in a postmenopausal pattern while a second woman was receiving an adequate dose since her hLHβcf profile returned to a premenopausal profile (see FIGS. 14A–14F).

The profile for patient LK (see FIGS. 14A–14B) revealed an area under the curve of 3050 before ERT and 1650 after ERT. The pre-ERT hLHβcf profile is similar to that observed for postmenopausal women. The reduction following treatment indicates that the ERT is somewhat effective. Patient LK exhibits an intermediate pattern after ERT treatment. The profile for patient VP (see FIGS. 14A–14B) displays an area under the curve of 1350 before ERT and 280 after ERT. This indicates ERT treatment was effective in reducing the amount of hLHβcf to an amount similar to the premenopausal pattern. The profile for patient NP (see FIGS. 14E–14F) revealed an area under the curve of 3200 before ERT and 3260 after ERT. This indicates that the ERT treatment was not effective in altering the amount of hLHβf. Patient NP continues to exhibit a profile similar to the the postmenopausal profile.

Example 3

Assessing Ovarian Function: Polycystic Ovarian Disease.

Blood samples were taken from women with polycystic ovarian disease (PCO). hLHβcf was detected in the blood of some of these patients. Furthermore, upon treatment with GnRH a rise in hLHβcf in the blood was measured. This could suggest a release of core fragment from the pituitary although a cross reaction might occur if the hLH concentration is very high. Thus hLHβcf which is not usually measureable in blood, can be detected in plasma after ethanol fractionation.

When PCO patients were treated with single injections of GnRH, Luprolite acetate (1 mg/dose), hLHβcf appeared in the serum. Thus, hLHβcf may have two origins, one directly from the pituitary and a second from peripheral degradation of circulating hLH (see Table VI). Unlike normal controls, some women with PCO have detectable hLH β core fragment in serum.

TABLE VI

| | Patients' Serum Concentration of hLHβcf/time after GnRH treatment | | | | | | | |
|---|---|---|---|---|---|---|---|---|
| pat. # | Urine. | 0h | 1 h | 2 h | 4 h | 8 h | 12 h | 24 h |
| 001a | 44[a] | 0[b] | ? | 4.6 | 12 | 10 | 14 | 6.8 |
| 001b | 38 | 0 | 4 | 6 | 10 | 12 | 8 | 4.8 |
| 002 | 30/32[c] | 0 | | | | | | |
| 003 | 26/26 | 0 | | | | | | |
| 004 | 260/280 | 0 | 0 | 0 | 8 | 12 | 10 | 0 |
| 006 | 360/320 | 0 | 0 | 0 | 4 | 6 | 4 | 0 |
| 007 | 76/80 | 0 | 0 | 0 | 0 | 0 | 0 | 0 |
| 008 | 50/40 | 0 | | | | | | |
| 009 | 240 | 14 | | | | | | |

[a]fmol/mg creatinine in urine;
[b]fmol/ml in serum c.

These studies are further supported by work with plasmapheresis fluid. The plasma of two postmenopausal patients undergoing this treatment was tested directly and found to exhibit no measurable levels of hLHβcf. However, after ethanol fractionation of the plasma and concentration (10×), high levels of the fragment was observed. In both patients, the fractionated plasma was gel filtered and the hLHβcf immunoreactivity appeared at its expected size of 10,000 M.W. Thus, at least some of this metabolite of hLH circulates in postmenopausal women, perhaps in a form complexed to another protein and only visible after dissociation by organic solvents.

This hLH fragment may circulate in blood, unlike the homologous hCG fragment which exists at very low levels in blood. Chromatographic separation of the pituitary hLHβcf as compared to the urinary molecule with the epitope recognized by our hLHβcf assay indicated that the urinary material eluted in a different position on reverse phase HPLC than did the pituitary form.

REFERENCES

Birken, S., E. G. Armstrong, M. A. Kolks, L. A. Cole, G. M. Agosto, A. Krichevsky, J. L. Vaitukaitis, and R. E. Canfield. 1988. Structure of the human chorionic gonadotropin beta-subunit fragment from pregnancy urine. *Endocrinology* 123:572–583.

Birken, S., Y. Maydelman, M. A. Gawinowicz, A. Pound, Y. Liu, and A. S. Hartree. 1996. Isolation and characterization of human pituitary chorionic gonadotropin. *Endocrinology* 137:1402–1411.

Birken, S., Y. Chen, M. A. Gawinowicz, J. W. Lustbader, S. Pollak, G. Agosto, R. Buck, and J. O'Connor. 1993a. Separation of nicked human chorionic gonadotropin (hCG), intact hCG, and hCG beta fragment from standard reference preparations and raw urine samples. *Endocrinology* 133:1390–1397.

Birken, S., M. A. Gawinowicz, A. Kardana, and L. A. Cole. 1991. The heterogeneity of human chorionic gonadotropin (hCG). II. Characteristics and origins of nicks in hCG reference standards. *Endocrinology* 129:1551–1558.

Birken, S., Y. Chen, M. A. Gawinowicz, G. M. Agosto, R. E. Canfield, and A. S. Hartree. 1993b. Structure and significance of human luteinizing hormone-beta core fragment purified from human pituitary extracts. *Endocrinology* 133:985–989.

Blithe, D. L., Akar, A H, Wehmann, R E and Nisula, B C. (1988) Purification of beta-core fragment from pregnancy urine and demonstration that its carbohydrate moieties differ from those of native human chorionic gonadotropin-beta. *Endocrinology* 122:173–180.

Burger, H. G. 1994b. Diagnostic role of follicle-stimulating hormone (FSH) measurements during the menopausal transition—an analysis of FSH, oestradiol and inhibin. [Review]. *Eur. J. Endocrinol.* 130:38–42.

Burger, H. G. 1994a. The menopause: when it is all over or is it?. [Review]. *Aust. N. Z. J. Obstet. Gynaecol.* 34:293–295.

Burger, H. G., E. C. Dudley, J. L. Hopper, J. M. Shelley, A. Green, A. Smith, L. Dennerstein, and C. Morse. 1995. The endocrinology of the menopausal transition: a cross-sectional study of a population-based sample. *J. Clin. Endocrinol. Metab.* 80:3537–3545.

Burger, H. G. 1996. The endocrinology of the menopause. [Review]. *Maturitas* 23:129–136.

Burger, H. G., P. G. Farnworth, J. K. Findlay, C. J. Gurusinghe, D. L. Healy, P. Mamers, A. Mason, and D. M. Robertson. 1995. Aspects of current and future inhibin research. [Review]. *Reprod. Fertil. Dev.* 7:997–1002.

Cole L A, Schwartz P E, Wang Y X 1988b. Gynecol Oncol 31:82–90

Cole L A, Wang Y, Elliot M, Latef M, Chambers J T, Chambers S K, Schwartz P E 1988a. Cancer Res 48:1356–1360

Cole L A, Nam J H, Chambers J T, Schwartz P E 1990 Gynecol Oncol 36:391–394 de Medeiros, S. F., F. Amato, and R. J. Norman. 1991. Stability of immunoreactive beta-core fragment of hCG. *Obstet. Gynecol.* 77:53–59.

Hee, J., J. MacNaughton, M. Bangah, and H. G. Burger. 1993. Perimenopausal patterns of gonadotrophins, immunoreactive inhibin, oestradiol and progesterone. *Maturitas* 18:9–20.

Iles, R. K., C. L. Lee, I. Howes, S. Davies, R. Edwards, and T. Chard. 1992. Immunoreactive beta-core-like material in normal postmenopausal urine: human chorionic gonadotrophin or LH origin? Evidence for the existence of LH core. *J. Endocrinol.* 133:459–466.

Kato Y. and Braunstein G. D. (1988) Beta-core fragment is a major form of immunoreactive urinary chorionic gonadotropin in human pregnancy. *J. Clin. Endocrinol. Metab.* 66:1197–1201.

Kovalevskaya, G., S. Birken, J. O'Connor, J. Schlatterer, Y. Maydelman, and R. Canfield. 1995. HLH beta core fragment immunoreactivity in the urine of ovulating women: a sensitive and specific immunometric assay for its detection. *Endocrine* 3:881–887.

Krichevsky, A., S. Birken, J. O'Connor, K. Bikel, J. Schlatterer, C. Yi, G. Agosto, and R. Canfield. 1991. Development and characterization of a new, highly specific antibody to the human chorionic gonadotropin-beta fragment. *Endocrinology* 128:1255–1264.

Krichevsky A, Birken S, O'Connor J F, Bikel K, Schlatterer J P and Canfield, R. E. (1994) The development of a panel of monoclonal antibodies to human luteinizing hormone and its application to immunological mapping and two-site assays. *Endocrine* 2:511–520

Lee, C. L., R. K. Iles, J. H. Shepherd, C. N. Hudson, and T. Chard. 1991. The purification and development of a radioimmunoassay for beta-core fragment of human chorionic gonadotrophin in urine: application as a marker of gynaecological cancer in premenopausal and postmenopausal women. *J. Endocrinol.* 130:481–489.

Metcalf, M. G., R. A. Donald, and J. H. Livesey. 1981. Classification of menstrual cycles in pre- and perimenopausal women. *J. Endocrinol.* 91:1–10.

Metcalf, M. G., R. A. Donald, and J. H. Livesey. 1982. Pituitary-ovarian function before, during and after the menopause: a longitudinal study. *Clin. Endocrinol. (Oxf).* 17:489–494.

Metcalf, M. G. 1979. Incidence of ovulatory cycles in women approaching the menopause. *J. Biosoc. Sci.* 11:39–48.

Metcalf, M. G., R. A. Donald, and J. H. Livesey. 1981. Pituitary-ovarian function in normal women during the menopausal transition. *Clin. Endocrinol. (Oxf).* 14:245–255.

Metcalf, M. G. 1988. The approach of menopause: a New Zealand study. *N. Z. Med. J.* 101:103–106.

Metcalf, M. G. and R. A. Donald. 1979. Fluctuating ovarian function in a perimenopausal women. *N. Z. Med. J.* 89:45–47.

Neven, P., R. K. Iles, C. L. Lee, C. N. Hudson, J. H. Shepherd, and T. Chard. 1993. Urinary chorionic gonadotropin subunits and beta-core in nonpregnant women. A study of benign and malignant gynecologic disorders. *Cancer* 71:4124–4130.

Neven, P., R. K. Iles, I. Howes, K. Sharma, J. H. Shepherd, R. Edwards, W. P. Collins, and T. Chard. 1993. Substantial urinary concentrations of material resembling beta-core fragment of chorionic gonadotropin beta-subunit in mid-menstrual cycle. *Clin. Chem.* 39:1857–1860.

O'Connor, J. F., J. P. Schlatterer, S. Birken, A. Krichevsky, E. G. Armstrong, D. McMahon, and R. E. Canfield. 1988. Development of highly sensitive immunoassays to measure human chorionic gonadotropin, its beta-subunit, and beta core fragment in the urine: application to malignancies. *Cancer Res.* 48:1361–1366.

O'Connor, J. F., S. Birken, J. W. Lustbader, A. Krichevsky, Y. Chen, and R. E. Canfield. 1994. Recent advances in the chemistry and immunochemistry of human chorionic gonadotropin: impact on clinical measurements. [Review]. *Endocr. Rev.* 15:650–683.

Santoro, N., J. R. Brown, T. Adel, and J. H. Skurnick. 1996. Characterization of reproductive hormonal dynamics in the perimenopause. *J. Clin. Endocrinol. Metab.* 81:1495–1501.

Schroeder, H. R. and Halter, C. M. (1983) Specificity of human beta-choriogonadotropin assays for the hormone and for an immunoreactive fragment present in urine during normal pregnancy. *Clinical Chemistry.* 29:667–671.

Stenman, U. H., J. M. Bidart, S. Birken, K. Mann, B. Nisula, and J. O'Connor. 1993. Standardization of protein immunoprocedures. Choriogonadotropin (CG). *Scand. J. Clin. Lab. Invest. Suppl.* 216:42–78.

What is claimed is:

1. A diagnostic kit for determining the onset of menopause for a female subject comprising:
   (a) an antibody which specifically binds to hLHβcf without substantially cross-reacting with hLH, hLHβ, or hCGβcf;
   (b) a solid matrix to which the antibody is bound;
   (c) reagents permitting the formation of a complex between the antibody and hLHβcf in a sample; and
   (d) a control sample selected from the group consisting of a sample from a premenopausal woman, a sample from a postmenopausal woman, and a sample from a man,
   wherein determining the onset of menopause using the diagnostic kit comprises measuring hLHβcf in at least three urine samples collected from the subject on consecutive days, beginning with the first day of menses.

2. The diagnostic kit of claim 1, wherein the antibody is B505, deposited with the American Type Culture Collection under ATCC Designation No. 12000.

3. The diagnostic kit of claim 1, further comprising a second antibody which is capable of binding to hLFβcf in the presence of the antibody of part (a).

4. The diagnostic kit of claim 3, wherein the second antibody is B503, deposited with the American Type Culture Collection under ATCC Designation No. 11999.

5. The diagnostic kit of claim 3, wherein the second antibody is labeled with a detectable marker.

6. The diagnostic kit of claim 5, wherein the detectable marker is a radioactive isotope, an enzyme, a magnetic bead, a dye or biotin.

* * * * *